United States Patent [19]

Korten et al.

[11] Patent Number: 4,972,842

[45] Date of Patent: Nov. 27, 1990

[54] METHOD AND APPARATUS FOR PRECISION MONITORING OF INFANTS ON ASSISTED VENTILATION

[75] Inventors: Jerome B. Korten, New York; Karl F. Schulze, Pelham, both of N.Y.

[73] Assignee: Vital Signals, Inc., New York, N.Y.

[21] Appl. No.: 204,460

[22] Filed: Jun. 9, 1988

[51] Int. Cl.[5] ............................................. A61B 5/08
[52] U.S. Cl. .............................. 128/716; 128/204.23; 128/200.24; 600/22
[58] Field of Search ........... 128/716, 720, 725, 200.24, 128/204.23, 202.22; 600/22

[56] References Cited

U.S. PATENT DOCUMENTS 4,671,297  6/1987  Schulze, Jr. .................... 128/716
4,750,474  6/1988  Dukhan et al. ................... 600/22

OTHER PUBLICATIONS

Reynolds et al., "A Multiplex . . . Plethymograph", Med. & Biol. Eng., vol. 11, No. 3, May 1973, pp. 268-274.
Comroe, Jr. et al., "Design of a Body Plethysmograph . . .", J. Appl. Phys., vol. 14, May 1959, pp. 439-444.
K. Schulze, et al., "Instrumentation for the Continuous Measurement of Gas Exchange and Ventilation of Infants During Assisted Ventilation," Critical Care Medicine, vol. 11, No. 11, pp. 892-896 (1983).
A. Greenough, et al., "Interaction of Spontaneous Respiration with Artificial Ventilation in Preterm Babies," Journal of Pediatrics 103:769 (1983).
Karl Schulze, et al., "Computer Analysis of Ventilatory Parameters for Neonates on Assisted Ventilation", IEEE Engineering in Medicine and Biology Magazine, vol. 3, No. 3, pp. 31-33, (Sep. 1984).
G. Gregory, et al., "Pneumotachograph for Use with Infants During Spontaneous or Assisted Ventilatino", Journal of Applied Physiology, vol. 31, p. 766 (Nov. 1971).
A. G. S. Philip, "Oxygen Plus Pressure Plus Time: the Etiology of Bronchopulmonary Dysplasia," Pediatrics, vol. 55, No. 1, pp. 44-50 (Jan. 1975).

Primary Examiner—Lee S. Cohen
Attorney, Agent, or Firm—Pennie & Edmonds

[57] ABSTRACT

An apparatus and method are disclosed for monitoring physiological parameters associated with the ventilation of infants during assisted ventilation. The infant is placed in a plethysmograph and various sensor means are used to measure flow of gas into and out of the plethysmograph and infant respiration. The outputs of the sensor means are supplied to a microcomputer system for processing. A unique calibration system is provided which constantly corrects for changing system parameters such as plethysmographic chamber air leaks, compliance and the like. Additionally, a heating system which exhibits radiant as well as convective heating properties is provided to maintain the infant in a constant temperature environment with a minimal amount of temperature fluctuation. From this data, ventilator breaths are discriminated from infant breaths.

44 Claims, 16 Drawing Sheets

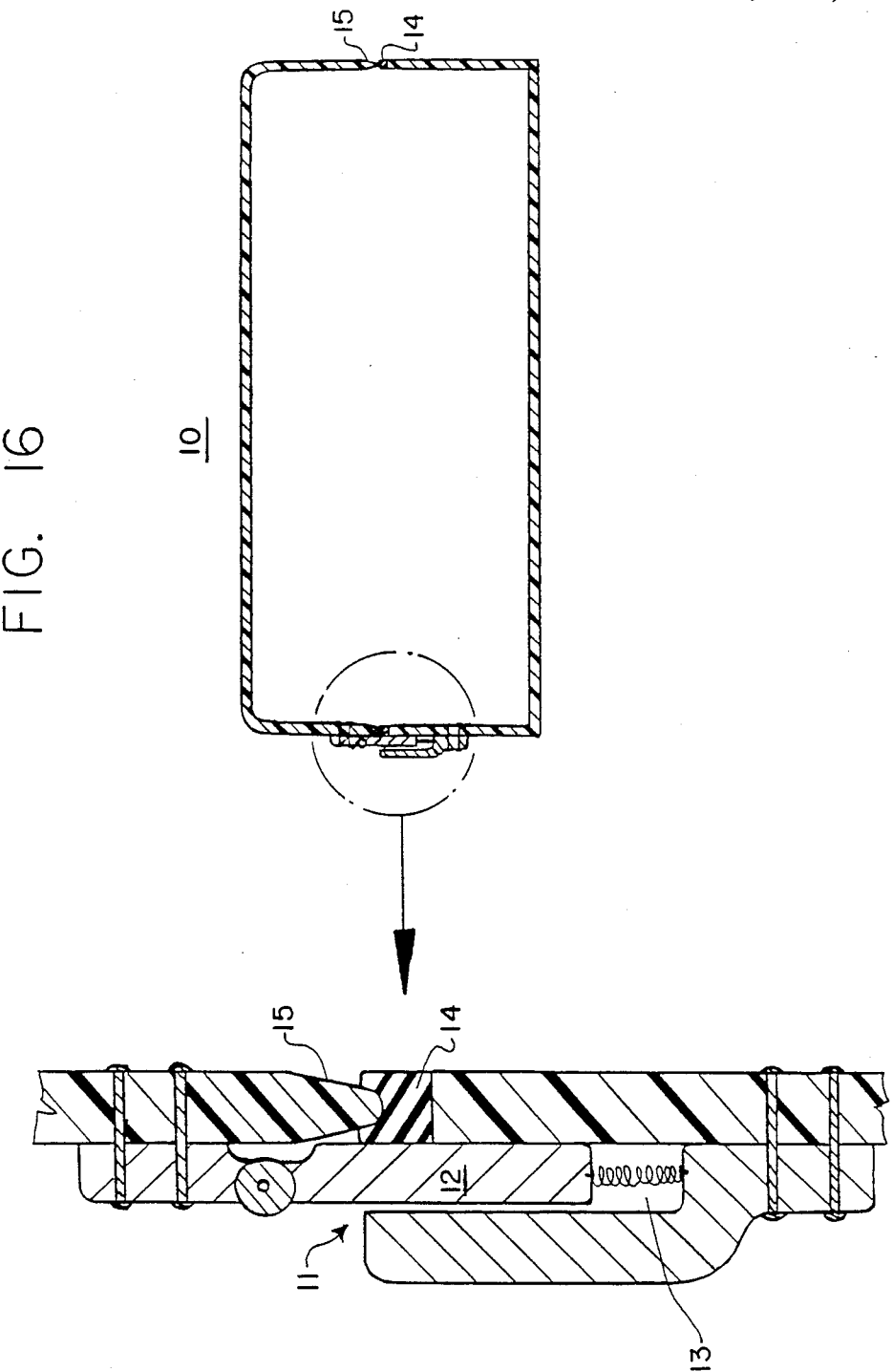

METHOD AND APPARATUS FOR PRECISION MONITORING OF INFANTS ON ASSISTED VENTILATION

BACKGROUND OF THE INVENTION

A portion of the disclosure of this patent document contains material to which a claim of copyright protection is made. The copyright owner has no objection to the electrophotographic reproduction by anyone of the patent document or the patent disclosure, as it appears in the Patent & Trademark Office patent file or records, but reserves all other copyright rights whatsoever.

Mechanical ventilatory assistance is now widely accepted as an effective form of therapy and means for monitoring respiratory failure in the neonate. Mechanical ventilators are a conspicuous and fundamental part of neonatal care. When on assisted ventilation, the newborn infant becomes part of a complex interactive system which is expected to provide adequate ventilation and gas exchange.

The overall performance of the assisted ventilatory system is determined by both physiological and mechanical factors. The physiological determinants, over which the physician has relatively little control, change with time and are difficult to define. These include the nature of any pulmonary disease, the ventilatory efforts of the infant, and many other anatomical and physiological variables. Mechanical input to the system, on the other hand, is to a large extent controlled and can be reasonably well characterized by examining the parameters of a ventilator pressure pulse. Optimal ventilatory assistance requires a balance between physiological and mechanical ventilation. This balance should insure that the infant is neither overstressed nor oversupported. Insufficient ventilatory support would place unnecessary demands on the infant's compromised respiratory system. Excessive ventilation places the infant at risk for pulmonary barotrauma and other complications of mechanical ventilation.

Intelligent management of ventilatory assistance in the neonate requires that information about the performance of the overall system be available to the clinician. Instruments for continuous monitoring of infants on assisted ventilation, as well as certain component variables of ventilation, are known and are discussed in "Instruments for the Continuous Measurement of Gas Exchange and Ventilation of Infants During Assisted Ventilation", K. Schulze, M. Stefanski, J. Masterson, L. S. James, *Critical Care Medicine*, Vol 11, No. 11, pp. 892–896 (1983), incorporated herein by reference. However, at the present time, physicians rely largely on intermittent measurement of arterial blood gases to monitor the overall effects of the system on gas exchange. These measurements, while important in clinical care, have several limitations. Data acquired by such measurements provides little information about the separate contributions of the infant and the mechanical ventilator to overall ventilation and gas exchange of the infant. It has also been recognized that mechanical ventilation, although potentially a very promising technique, may indeed be harmful to the lungs and brain of the infant in the event that the mechanical ventilator is not properly synchronized with the infant's breathing. For example, see A. Greenough, C. Morley, J. A. Davis, "Interaction of Spontaneous Respiration with Artificial Ventilation in Pre Term Babies", Journal of Pediatrics 103:769 (1983). Furthermore, difficulty has been encountered in calibrating known systems to provide accurate and precise measurements of flow rates and the like.

Absent information concerning the respective contributions of ventilation, the effects of changes in ventilator support are not as readily observable. For example, it is frequently desirable to monitor how an infant responds to respiratory therapy such as positive end expiratory pressure ("PEEP") therapy. To administer this therapy, the ventilator decreases resistance to expiratory gases, thus decreasing the burden on an infant's lungs.

In addition, arterial blood gas measurements are available only intermittently in known systems. Unfortunately, this makes both trends and abrupt changes in clinical condition of the patient difficult to recognize. Continuous values are appreciably more helpful in describing the time course of changes in the patient's clinical condition than instantaneous or intermittent values.

When acquiring measurements of infant ventilation for research purposes, it is customary to place the infant in a container known as a plethysmograph. A plethysmograph is a standard device for measuring change in volume of any mass contained within it. Because changes in volume of animals or humans are due entirely to the flow of gas into and out of the lungs this device affords an elegant approach for the measurement of pulmonary function.

Normally, a plethysmograph is configured as an airtight box enclosing a subject who breathes externally supplied gas directly through an endotracheal tube inserted into the subject's nose, through his throat and into his windpipe. Thus, any gas breathed by the subject must be supplied from and exit via appropriate portions of the endotracheal tube and related piping. This gas breathed by the subject is supplied from a gas source and does not communicate with air contained within the plethysmograph. As the subject inspires, the volume of the chest increases and causes either the pressure to rise inside the plethysmograph chamber if it is closed or, if the plethysmograph chamber has an opening, air to flow out, or a combination thereof. These changes in pressure or flow can be measured using any of a variety of sensors. With the exception of openings used for respiratory support of the infant, and quantitative measurement of the infant's respiration, the interior of the plethysmograph must be isolated from the external environment. Also, for these quantitative measurements to be useful in patient care, it is desirable to configure the plethysmograph such that the sensors are in a relatively stable environment. At the same time, however, it is essential that the infant remain warm and undisturbed and also be accessible in a very short period in the event that an emergency arises.

Unfortunately, accuracy of measurements made by known plethysmographs is severely compromised by the inherent compliance of air contained within the plethysmograph, as well as compliance of elements such as tubes within the plethysmograph and the resistance of openings through the plethysmograph. As will be appreciated, volumetric displacement of gas caused by an infant's breathing is not measured directly, rather, the air expelled from the interior of the plethysmograph through a resistive opening(s) through a wall of the plethysmograph is quantitatively measured. Although an infant's inspiration of gas will result in the expiration of air through the resistive opening in the plethysmograph (caused by a change in the volume of the infant), such inspiration will also tend to increase the pressure of air within the plethysmograph due to the resistivity of the opening, typically a fine mesh type structure, to gas flow. Similarly, expiration of gas from the infant's lungs will cause inspiration of air through the resistive opening accompanied by a decrease in the pressure within the plethysmograph. As a result, the quantity of gas expired/inspired by the infant's lungs and the quantity of air inspired/expired by the plethysmograph are not equal, thereby introducing another source of error which limits the accuracy and precision which may be achieved by known plethysmographs.

Additionally, leakage through various portions of the plethysmograph contribute to the introduction of error in calculations for determining flow rates and volumetric displacement. For example, leakage through the large seals which separate two halves of the plethysmographic chamber has been found to be a common source of error.

An additional deficiency of known plethysmographs is their inability to maintain a constant temperature environment for the infant. This disadvantage is also shared by other devices such as an incubator whose very purpose is to maintain a constant temperature environment for the infant. A constant temperature environment is critical to the survival of infants and, in particular, of premature infants.

Known incubators and/or plethysmographs generally attempt to maintain a constant temperature environment by either one of two methods, namely, by radiant heating or by convective heating. A typical radiant heater comprises a heat source such as a light source of appropriate wavelength radiating heat energy towards an exposed infant. A typical convective heater comprises a heating coil and, optionally, means for transporting air heated by such coil to the infant. Unfortunately, neither of these two methods has been found entirely satisfactory in maintaining a constant temperature environment for the infant.

SUMMARY OF THE INVENTION

In accordance with the present invention, a method and apparatus are described herein for providing continuous measurement of infant ventilation during assisted ventilation, which is particularly adapted for providing a precise determination of flow rates and volumetric displacement occasioned by an infant's breathing. In addition, means are provided for maintaining a highly constant temperature environment for the infant. Information is also available regarding the respective contributions to ventilation by the infant and the ventilation mechanism.

In the presently preferred embodiment, the apparatus comprises a plethysmographic chamber in which an infant is placed, a pneumotachometer and a differential pressure transducer for detecting infant respiration, a pressure transducer for measuring pressure in a respirator tubing portion of an endotracheal tube inserted into an infant's airway in order to discriminate the infant's breaths from ventilator breaths, an environment temperature control system for maintaining a constant temperature environment within the plethysmograph, means for precisely and constantly correcting for error introduced by the compliance of the system and leakage through the plethysmograph, means for determining the gain of the plethysmograph, and a preprogrammed microcomputer system for processing and storing data acquired by the aforementioned components. In another embodiment, the invention comprises a second pneumotachometer and a second differential pressure transducer for determining when ventilator breaths occur.

Details of the performance of a known plethysmograph are described in Karl Schulze, et al., "Computer Analyses of Ventilatory Parameters For Neonates On Assisted Ventilation," *IEEE Engineering In Medicine And Biology Magazine* Vol. 3, No. 3, pp. 31-33 (Sept. 1984) and U.S. Pat. No. 4,671,297 to Schulze which are each expressly incorporated herein by reference.

In an alternate embodiment, data from the differential pressure transducer and from the airway pressure transducer or second differential pressure transducer are processed off-line.

In accordance with the invention, accurate measurement of flow rates is possible through the use of a calibration system which constantly corrects for leaks in components of the plethysmograph as well as its compliance. The flow rate corrected due to errors introduced by the compliance is calculated by adding a first correction factor onto the measured flow rate. This first correction factor is proportional to the time constant of the plethysmographic chamber, namely, the resistance of an airflow opening in the chamber multiplied by the compliance of the air inside the box. Since the compliance of such air is affected by the volume of the infant, calculation of the compliance is advantageously performed in real time, while the infant is in the chamber. Furthermore, by constantly updating the time constant, extremely accurate and precise measurements can be made.

Additionally, calculation of pneumotograph gain provides an additional correction factor which can be used to increase the accuracy and precision of calculated flow rates. Application of a pressure pulse of known volume to the plethysmographic chamber results in detection of a measured volume of air expelled out of the chamber. The ratio of the known volume of the pressure pulse to the measured volume of air expelled is a measure of the gain of the chamber. Through appropriate signal processing, the most current gain calculation is available to be used as a second correction factor to be applied to measured flow rates. While the first correction factor may be viewed as a frequency correction factor, the second correction factor may be viewed as an amplitude correction factor.

An additional feature of the present invention is that the plethysmograph, which is ordinarily utilized as a research tool, is adapted for clinical patient care. The plethysmographic chamber is provided with means for maintaining a very constant temperature environment and advantageously functions not only as a plethysmograph but additionally as an incubator. Furthermore, the data obtained through real-time monitoring of physiological parameters and responses to stimuli is of great clinical value. Additionally, due to the mobility of the present invention, it is suitable for use in an operating room, x-ray suite and other such areas of a hospital where intensive care is not currently available.

BRIEF DESCRIPTION OF THE FIGURES

These and other objects, features and advantages of the invention will be more readily apparent from the following detailed description of the preferred embodiment in which:

FIG. 16 depicts a plethysmograph of the present invention, including a "tongue-in-pocket" hinge means and gasketing material.

DETAILED DESCRIPTION OF THE PREFERRED EMBODIMENT

Figure 1:
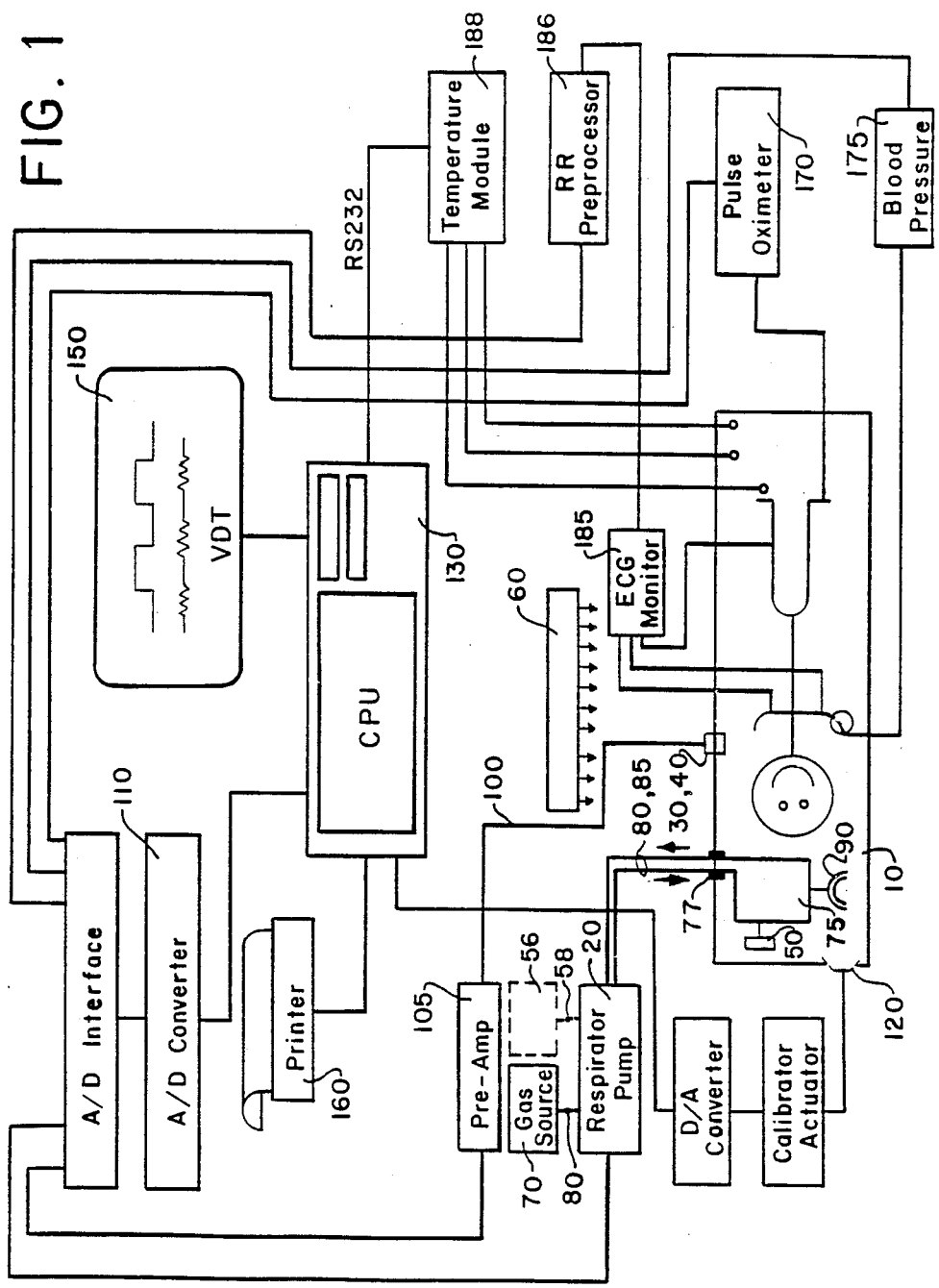
FIG. 1 is a block diagram showing an overview of the presently preferred embodiment of the apparatus as employed in a system for ventilating an infant.

As depicted in FIG. 1, the presently preferred embodiment of the apparatus comprises a plethysmograph 10 in which is placed an infant to be monitored, a ventilator such as a respirator pump 20 for ventilating the infant, a pneumotachometer 30 and a differential pressure transducer 40 for measuring gas flow into and out of plethysmograph 10, a pressure transducer 50 for detecting pressure in the infant's airway, means 60 for maintaining a constant temperature environment and a pressure pulse source 120. A gas source 70 feeds ventilator 20 via pipe 80 with gas for ventilation of the infant. This gas, typically an oxygen-nitrogen mixture, is provided to the infant in the plethysmograph 10 through pipe 75 and an endotracheal tube 90. Illustratively, pipes 75, 80 are coupled together at port 77. Pipe 85 carries expiratory gases back to ventilator 20. When ventilator 20, illustratively a Healthdyne model 100 ventilator, fires to respirate the infant, the ventilator occludes pipe 85 so that gas provided to the infant by pipes 75, 80 will be forced through endotracheal tube 90 and into the infant's airway.

Analog data provided by differential pressure transducer 40 is provided to a microcomputer system 130 by line 100. Pressure transducer 50 also provides microcomputer system 130 with analog data by a line (not shown). Computer 130 digitizes this analog data from transducers 40 and 50 and processes it to obtain total tidal volume, volume due to infant respiratory efforts and volume due to the effects of mechanical ventilation. These values are then displayed by the microcomputer on a suitable video display terminal (VDT) 150. Illustratively, this display unit provides both digital and analog displays and a printer 160 provides a nursing report or a hard copy of the VDT display. Advantageously, all of the equipment depicted in FIG. 1 is mounted on a movable cart so that the infant can readily be moved, for example, for emergency treatment, without adversely affecting either the infant's respiratory support or the monitoring thereof. Appendix I of this specification provides suitable object code for execution on microcomputer system 130.

In the presently preferred embodiment, plethysmograph 10 comprises a plexiglass plethysmographic chamber or box, capable of containing an infant. The interior atmosphere of the plethysmograph is isolated from the exterior environment, except for one or more ports necessary for respiration of the infant, i.e., port(s) for pipes 80, 85.

Plethysmograph 10 is depicted in FIG. 16 and preferably comprises a plexiglass box which has been split in half. The top is hinged along one side and soft rubber gasketing material is applied along the edges of the top and bottom such that when the top closes a very tight seal is formed. Although this seal is nearly air-tight, access to the infant is quite easy since the plethysmograph top need only be swung to the open position. The hinge means is constructed using a "tongue-in-pocket" design 11 having tongue means 12 and pocket means 13 so that on the rare occasions when it is required, the entire top of the plethysmograph lifts off allowing access from both sides of the infant. The hinge means preferably provides for a certain degree of vertical movement in the area where it is attached to the two halves so that the gasket material there is not pinched or otherwise misaligned. Alternatively, only the bottom half of the plethysmograph is provided with a suitable gasketing material 14 and the top half of the preferably plexiglass box is provided with a tapered edge 15 to mate and seal with the gasketing material of the lower half of the box. Even though very little air escapes at the junction between the top and bottom halves of the box, a method for performing repeated calibrations of the box, while the infant is in it, will correct for any leaks. This method provides a means of making frequent measurements of key parameters which, in turn, make measurements of gas flow into and out of the infant's chest extremely accurate.

Advantageously, the plethysmograph accommodates monitoring leads, intravenous tubes and the like through sterile adaptors that fit into the wall of the plethysmograph.

Pneumotachometer 30 illustratively comprises a pliable and semi-permeable screen, opposite sides of which, at times, are exposed to different pressure levels. Pneumotachometer 30 communicates with and receives air flow through an opening in a wall of the plethysmographic chamber. Although many appropriately selected commercial pneumotachometers will be suitable for use in the practice of the invention, a preferred pneumotachometer comprises a screen structure such as a 400 mesh pneumotachometer. This device provides a known resistance to air flow and is exposed on one side to the interior of the plethysmograph and on the opposite side to the exterior. Alternatively, a description of another suitable pneumotachometer may be found in "Pneumotechograph For Use With Patients During Spontaneous or Assisted Ventilation," G. Gregory, J. Kitherman, *Journal of Applied Physiology*, Vol. 31, p. 766 (Nov. 1971).

Air flow into and out of the plethysmograph is computed by monitoring the pressure difference across a known resistance provided by pneumotachometer 30. Pressure variations occurring on the interior of the plethysmograph, such as those resulting from expansion and contraction of an infant's chest, are reflected by a pressure drop across the pneumotachometer. Pneumotachometer 30 serves to provide a pressure differential between the interior of the plethysmograph and the exterior environment by creating a resistance to air flow. This pressure differential is measured by differential pressure transducer 40 which has a first port communicating with the interior of plethysmograph 10 and a second port communicating with the external environment. The ventilatory flow signal is computed from the pressure differential. These two ports of differential pressure transducer 40 are separated by pneumotachometer 30. Alternatively, a separate opening through the wall of the chamber for pneumotachometer is not necessary if there is sufficient leakage elsewhere in the plethysmograph. For example, if the seals between the two halves of the chamber leak, a suitable pressure difference between the interior and the exterior of the chamber may develop and be measured by transducer 40; in this situation, a separate pneumotachometer is not necessary as the leaking seals or the like may suffice.

Alternatively, pneumotachometer 30 and differential pressure transducer 40 may be located inside the plethysmograph, with a port of the pneumotachometer open to the plethysmograph interior. Placement of pneumotachometer 30 and transducer 40 inside the plethysmograph may reduce the potential for inaccuracies in the data acquired due to temperature differences between said elements and the plethysmograph, although placement of pneumotachometer 30 through a wall of the chamber generally provides a better signal to noise ratio. Differential pressure transducer 40 senses the pressure on the two sides of pneumotachometer 30 and outputs an analog signal to line 100 showing the amount and direction of gas flow into and out of plethysmograph 10. Illustratively, the pressure transducer is a variable reluctance type that is driven at 5 KHz by a carrier-demodulator preamplifier 105. A suitable differential pressure transducer and preamplifier comprises pressure transducer model number MP-45-871 available from Validyne Engineering, Inc. and preamplifier model number CD-15-871 also available from Validyne. The analog signal output by pneumotach preamplifier 105 is interfaced with computer 130 and is preferably digitized at 50 samples per second by an A/D converter 110.

In the presently preferred embodiment, the amount and direction of gas flow are reflected by the magnitude and polarity, respectively, of the output signal from transducer 40. Thus, inspiration and expiration result in different polarity outputs from the transducer.

Pipe 75 is coupled to endotracheal tube 90, which is in turn inserted into the airway of the infant. Pressure transducer 50 is located in the endotracheal tube and senses pressure in the infant's airway. Transducer 50 outputs an analog signal indicating such pressure and provides such output to computer 130 by way of A/D converter 110, which illustratively samples at 50 samples per second. Pressure transducer 50 is preferably a Novametrix Pneumogard Model 1200 pressure transducer. In an alternate embodiment the function of pressure transducer 50 is instead accomplished by a second pneumotachometer and pressure transducer 56. These components detect pressure changes in pipe 58.

Airflow into and out of the plethysmograph is computed from the pressure differences measured across the resistance to airflow provided by pneumotachometer 30. This pressure drop is directly proportional to the airflow. Subsequent integration of the flow measurements provides a direct measure of the volume of air that flows through the pneumotachometer. Since airflow in and out of the box is caused by chest wall expansion and contraction these volume measurements provide a highly accurate measure of inspired and expired air volume with each breath, regardless of whether these breaths were generated by the infant or the ventilator.

More specifically, the zero flow point for the pneumotachometer is constantly calculated and provided to the computer. Zero crossing in the positive direction coupled with a positive slope threshold detection are used to determine when a positive airflow that is due to inspiration exists. In a similar fashion zero crossing in the negative direction coupled with a negative slope threshold detection is used to determine when expiration occurs. In addition, once a breath has been identified, it must fall within predefined limits for volume and duration before it is included for analysis. A real time moving average filter and differentiator is employed and provides for accurate and precise measurements.

Means 60 for maintaining a constant temperature environment permits utilization of plethysmographic chamber 10 as an incubator. A desired temperature level is accurately and precisely maintained by combining radiant heating with convective heating, yielding a heating system with a minimal amount of temperature fluctuation. Preferably, means 60 comprises a radiant heater mounted external to the plethysmograph and radiating heat towards the plethysmograph. Such radiated heat travels through the translucent plethysmograph and is absorbed by the skin of the infant. Simultaneously, the interior of the plethysmograph is convectively warmed by the contact of interior air with the heated portion of the plethysmograph exposed to the radiant heat of the heater. Thus, the interior of the plethysmograph will generally be at a higher temperature than the external environment due to this double-stage heating employing radiant as well as convective heating aspects. This combined effect of warming by both radiant and convective mechanisms allows temperature to be maintained at a given level with less fluctuation than is normally associated with conventional radiant warmers. Studies have been performed on a large number of low birth weight infants and indicate that the metabolic rates of infants in this system are not different from those cared for in either pure convective or pure radiant heating systems.

Alternatively, heating means 60 may comprise, either alone or in combination with radiant heating and/or convective heating, heating elements directly incorporated into the wall(s) of the plethysmograph, similar in form to defrosting systems typically employed in rear windows of automobiles. Advantageously, such heating elements require a relatively small amount of current to properly heat a plethysmograph. In such an alternative embodiment, the heat flow will be regulated by a servomechanism coupled to temperature probes within the plethysmograph and on the infant's skin.

Microcomputer 130 and associated hardware performs on-line computations of ventilatory parameters, collects and integrates information available from physiologic monitors such as pulse oximeter 170, blood pressure transducer 175, temperature module and sensor 180 and ECG monitor 185. The computer derives relationships among variables and parameters from these monitors, displays graphic outputs of the analyses, records the data into disk files for later retrieval, and produces written hard copy reports. A preferable computer is the AST Premium Computer which is designed around the Intel 80286 microprocessor and 80287 math co-processor. It is configured with 640 kilobytes of random access memory, a 40 megabyte hard disk drive, a 1.2 megabyte floppy disk drive, and a Yamaha PCDC II graphic controller.

Temperature module and sensor 180 are used to monitor the chamber wall and air temperature. More particularly, temperature is continuously recorded at a number of sites. These sites include the patient's skin, ambient air, and two surfaces of the incubator. These data are plotted on the temperature display for retrospective review of the thermostability of the patient and the environment. A suitable temperature monitor is model 208 available from Cryotronics, Inc. This monitor is coupled to computer 130 by way of an RS232 interface which has been modified for proper transmission of date (pins 4 and 5 are connected to each other, pins 6, 8 and 20 are connected to each other, pins 2 and 3 are reversed).

ECG monitor 185 may be any of a number of commercially available electrocardiogram monitors. Electrocardiogram preprocessor 186 is used to determine the beat to beat interval of each heartbeat. This interval is timed to the nearest tenth of a millisecond.

More particularly, the preprocessor is an electronic "front-end" ECG preprocessor available from K & M Interface, Inc. of New York which detects the times when R-waves reach their peak and computes the interval between successive R-waves with a resolution of ±0.1 msec. The computer receives RR intervals from the preprocessor over a parallel port and uses these to compute instantaneous heart rate. The beat-to-beat rates are plotted sequentially on a cardiorespiratory display along with blood pressure and tidal volume. In addition, the mean heart rate is computed each minute and logged in the date base and these means are used for display in the trend screen and archival storage on disk.

Advantageously, circular buffers are used for the storage of heart rate information. In this way, continuous scrolling of the graphic data, from right to left, can be achieved without the necessity of moving large amounts of data in memory.

Advantageously, the present invention permits online assessment of heart rate variability. Estimates of "long-term" and "short-term" heart rate variability, defined as the coefficient of the change in RR intervals, (standard deviation of RR interval/mean of RR interval) and the coefficient of variation of the RR intervals (standard deviation of difference in adjacent RR intervals/mean of difference in adjacent RR intervals), respectively, are computed each minute and are stored in the data base. In addition, a fast Fourier transform (FFT) power spectrum analysis of each successive set of 128 RR-intervals is performed. From these analyses the contribution to overall heart rate variability that are associated with specified frequencies are then summed. One frequency band over which power is summed are the frequencies that encompass ±1 standard deviation of the respiratory rate that was computed during the relevant 128 beat interval. This portion of heart rate variability, which is coupled to breathing activity, is referred to in the art as respiratory sinus arrhythmia. This measure is believed to arise solely from variations in vagal nerve activity which regulates cardiac timing. This indirect measure of autonomic nervous system influence on the heart offers an innovative tool for examining the integrity of brain mechanisms that influence cardiorespiratory function.

In the presently preferred embodiment, precision and accuracy are maintained by constantly correcting for errors introduced by compliance and leakage of the system. In particular, compliance of the air within the plethysmograph and of other compliant elements such as tubing within the plethysmograph as well as the resistance of the pneumotachometer to air flow contribute to inaccurate measurements unless they are properly compensated for. Factors such as the size of an infant will affect the total compliance of the system and the rate of air flow and must be compensated for on a case by case basis. As will be appreciated, an accurate determination of the frequency response of the plethysmograph will aid in the calculation of flow rates which are corrected due to the compliance of the system.

Theoretically, the frequency characteristics of the plethysmographic system may be modelled as a first order low pass filter. In this case the response to an abrupt change in pressure provides information about the time constant of the plethysmograph. In particular, the time constant (TC) of the plethysmograph is the inverse of the resistance to flow multiplied by the compliance (1/RC). The time constant can be derived from the decay rate of flow following application of a stepped change in pressure. This is done by modelling the decay as an exponential of the form:

$$Y(t) = A * exp(-k * t) \tag{1}$$

where Y(t) is the flow measured at time t after the step change in pressure, A is the initial flow, i.e., peak flow, and k is the inverse of the time constant. By sampling the decay curve at frequent intervals, equations can be created that allow for a simultaneous solution for the two unknowns, namely A and k.

$$y_1 = A * exp(-k * t_1) \tag{2}$$

$$y_2 = A * exp(-k * t_2) \tag{3}$$

rearranging each equation, $$A = y_1/(exp(-k * t_1)) \tag{4}$$

$$A = y_2/(exp(-k * t_2)) \tag{5}$$

thus, $$y_1/(exp(-k * t_1)) = y_2/(exp(-k * t_2)) \tag{6}$$

taking the log of both sides, $$LN(y_1) - LN(\exp(-k * t_1)) = LN(y_2) - LN(\exp(-k * t_2)) \quad (7)$$

$$LN(y_1) - (-k * t_1) = LN(y_2) - (-k * t_2) \quad (8)$$

$$LN(y_1) - LN(y_2) = (-k * t_1) - (-k * t_2) \quad (9)$$

$$LN(y_1) - LN(y_2) = k * (t_2 - t_1) \quad (10)$$

thus, $$k = (LN(y_1) - LN(y_2))/(t_2 - t_1) = 1/TC \quad (11)$$

Substitution of k into either equation (4) or (5) will yield a value for A. Once a value for TC is known, flow can be corrected by multiplying the time constant times the first derivative of flow and adding this to the flow signal. That is, $$\text{frequency corrected flow} = \text{measured flow} + TC * d(\text{measured flow})/dt \quad (12)$$

Equation (12) is a formula known in the pertinent art and useful herein for calculating a frequency corrected actual flow rate from a measured flow rate and knowledge of the proper time constant.

In this way, the frequency response of the plethysmograph (which is normally down 3 db at 2 Hz) can be extended well beyond 5 Hz providing unprecedented accuracy in real-time measurements of flow through a plethysmographic system. Although actual respiration rates rarely exceed 2 Hz, such an increase in frequency response provides a substantial increase in accuracy since respiration is not purely sinusoidal but, rather, contains many higher order frequencies.

As will be appreciated, the time constant (TC or R*C) comprises two terms, the resistance of the airflow opening (R) and the compliance of the air inside the box (C). Changes in the measured time constant reveal information about the change in the leakage and/or compliance of the box. Since the box compliance is dependent upon the volume of air in the plethysmograph, and hence on the volume of air displaced by the infant within the plethysmograph, the measured time constant will change with different size infants which displace different volumes from within the plethysmograph. Therefore, it is critical to be able to measure the time constant of a whole body plethysmograph in order to obtain accurate results. Moreover, since the time constant is dependent on the size of the infant within the plethysmograph, the time constant must be measured while the infant is inside the plethysmograph.

In the preferred embodiment of the invention, determination of the time constant of a whole body, i.e., including infant and plethysmograph, in order to ultimately calculate the corrected flow rate from the measured flow rate, comprises three steps, namely, 1. Extraction Of A Decay Response To A Step Change In Volume.
2. Determination Of The Maximum Value Of The Transient Wareform.
3. Calculation Of The Time Constant.

Step 1: Extraction Of A Decay Response To A Step Change In Volume

Referring again to FIG. 1, pressure pulse source 120 is the means by which a step change in volume is produced. More specifically, pulse source 120 preferably comprises a linear displacement actuator in the form of a modified polypropylene audio speaker which is optimized for suitably high rates of acceleration. The displacement actuator is housed within a plexiglass box (not shown) or the like so that a minimum volume of air is contained between the actuator surface and the inside of the plethysmographic chamber. The connection between the displacement actuator and the plethysmographic chamber is through a hole in the wall of the plethysmographic chamber. In alternate embodiments, the connection is made through a high resistance, i.e., small, hole in order to decouple the compliance of the two systems when the pulse source is not in use. The displacement actuator is stepped in and out by a high accuracy power amplifier module (not shown) available from K&M Interface, Inc. of New York. When the displacement actuator is stepped in the positive direction, injecting air into the plethysmographic chamber, there is a transient pressure increase that rapidly decays. This decay rate is measured and taken as the time constant of the system.

As will be appreciated, since the system must measure the time constant in the presence of an infant, the step response to the displacement actuator must be separated from the breathing movements of the infant. For this, a signal averaging algorithm is preferably employed. The displacement actuator is repeatedly stepped in and out, providing transient pressure increases and decreases. The decreases are preferably inverted rendering these waveforms identical to those which follow the transient increases. This allows the transient decreases to be averaged along with the transient increases providing twice as many events for signal averaging. Illustratively, for an infant respiration rate of 60–80 breaths per minute and a volumetric displacement of 5 cc per kilogram of infant weight, a step pulse of 60 cycles per minute and a volumetric displacement of 80–100 cc has been found suitable.

Step 2: Determination Of The Maximum Value Of The Transient Waveform

The maximum value of the transient waveform is the start of the exponential decay, i.e., the variable A in equations (3) and (4). This value is determined using amplitude analysis by locating the local maximum of the step response. Once the start of the decay period is determined, a following portion of the decay (until the step response is reversed) is included in the analysis according to the previously enumerated equations. A portion of approximately 80% of the decay has been found suitable.

Step 3: Calculation Of The Time Constant

Repeating equation (11), it is seen that:

$$k = (LN(y_1) - LN(y_2))/(t_2 - t_1) = 1/TC \quad (11)$$

However, if only two points are sampled ($y_1$ and $y_2$), the measurement is subject to substantial error from noise. Therefore, a plurality of such points are preferably utilized to accurately calculate the value k as follows. First, the decay curve is log-linearized and then least squares linear regression is performed on a plurality of data points to estimate the slope of the linearized decay, namely, the value k. Any suitable number of such points may be utilized with fifty such points having been found suitable.

Thus, determination of the time constant in the above manner enables calculation of the frequency corrected flow rate in accordance with equation (12). As will be discussed in conjunction with FIG. 8, this method provides for very accurate and precise determination of the time constant.

As will be appreciated by one skilled in the art, calculation of actual, as opposed to relative, volumetric displacements and flow rates is only possible by knowing the gain of the system, i.e., the pneumotachograph gain. The known volume of air injected by the pressure pulse source provides the means for calculating this gain.

More specifically, the gain of the pneumotachograph can be determined when the average response to the displacement actuator is known. This is because a constant and known volume is injected into and withdrawn from the plethysmographic chamber on each cycle of the actuator. The volume injected is measured by integrating the flow signal at the pneumotachometer during the step response. This measured volume is compared to the known volume displaced by the pulse source. The gain of the system is then determined by the ratio of measured to actual volume (Vact/Vmeas).

Thus, the "gain-corrected" flow is given by:

$$\text{gain-corrected flow} = \text{measured flow} * (V_{act}/V_{meas}) \quad (13)$$

Therefore, the actual flow is given by either of the following formulas:

$$\text{actual flow} = \text{gain-corrected flow} + TC * d(\text{gain-corrected flow})/dt \quad (14)$$

or $$\text{actual flow} = \text{frequency-corrected flow} * (V_{act}/V_{meas}) \quad (15)$$

In the presently preferred embodiment, the output signal of differential pressure transducer 40 is positive during inspiratory flow and negative during expiratory flow. Ideally, the integration of positive value inspiratory flow data should equal the integration of negative expiratory flow data, since, over time, the volume of gas into and the volume of gas out of the infant's lungs are ordinarily the same. To obtain a calibration factor to compensate for the difference between measured inspiration volume and measured expiration volume, a predetermined amount of flow data obtained during a recent sample injection and withdrawal of gas is integrated. A bias value is derived during the calibration process which is obtained by calculating the mean flow of the positive and negative step responses. Advantageously, the bias value is constantly updated and represents a moving average, thereby providing a highly current and accurate dynamic bias value.

Next, the positive inspiratory data, only, are integrated, with the bias value being subtracted from each sample of flow data as it is included in the integration computation. The volume of gas which was injected in this calibration procedure, in cubic centimeters, is then divided by the adjusted integration to determine the calibration factor. The data obtained during monitoring is then processed.

Advantageously, this calibration factor, like the bias value, is constantly updated and represents a moving average, thereby providing a highly current and accurate calibration factor. Since such calibration is performed utilizing data gathered over a period of time, irregularities occurring within one or two breaths are not mistaken for a general inaccuracy in measurement.

In this embodiment, the predetermined volume of gas injected into and withdrawn from plethysmograph 10 is sufficiently large such that ventilator and infant breaths will comprise a relatively small percentage of total flow. A predetermined amount of flow data obtained from transducer 50 during injection and withdrawal is integrated and a real-time bias value is then obtained by dividing this integration by the product of the number of flow data samples obtained and the sampling rate. This real-time bias value is an index of the degree to which inspiration and expiration differ, and is useful to physicians as an estimate of such factors as endotracheal tube leakage and thermal transients. Optionally, the real-time bias value also serves as an alarm indicator when the endotracheal tube is leaking or is slipping from the infant's airway. The bias value also gives the physician an indication of the stability of the monitoring system.

It is anticipated, however, that some flow data which appears to represent breaths will actually be the result of factors other than respiratory activity. Movement by the infant, for example, may generate such flow data. In order to obtain an accurate measurement of breath tidal volume, actual breath must be discriminated from noise. Illustratively, the flow data acquired during the relevant period is tested to determine whether it meets the following criteria: the data contains only two polarity changes, a negative-to-positive polarity change followed by a positive-to-negative polarity change; the flow data must indicate that the breath was of at least a minimum duration and a minimum tidal volume; and the highest value data point of the flow data must be of at least a minimum value.

In the presently preferred embodiment, the criteria for a valid breath, either ventilator induced or infant, are that it must be at least 0.1 seconds in duration and must result in a tidal volume of at least 0.5 cubic centimeters.

Tidal volume of valid breaths is computed by integrating the inspiratory flow data obtained during those breaths and multiplying the result by the calibration factor. Illustratively, for each minute of monitoring, the tidal volume, duration and maximum amplitude of each inspiratory volume or breath and the total tidal volume and frequency of breaths are stored in a memory file for minute total data.

In accordance with the present invention, the minute total data is indexed to and processed in conjunction with pressure data from pressure transducer 50 to determine whether each breath is the result of infant respiratory efforts or is due to mechanical ventilation. For each minute of monitoring, tidal volume of each breath is referenced to airway pressure data obtained from pressure transducer 50 during the same period. More particularly, under control of the computer program set forth in Appendix I, microcomputer system 130 compares each inspiratory volume, within a given minute, with the airway pressure data obtained from pressure transducer 40, or alternatively with the data output by second transducer 56, during the period that the inspiratory volume was collected.

The data associated with a given breath is input to microcomputer system 130 to determine whether the inspiratory volume associated with that data was due to an infant breath or resulted from mechanical ventilation. An inspiratory volume which occurs simultaneously with a change in airway pressure which exceeds a predetermined magnitude is considered to relate to a mechanical ventilator breath. In the presently preferred embodiment, the predetermined change in airway pressure is approximately 20 mm. of Hg., but this value is subject to change depending upon the ventilator output pressure. Conversely, a breath occurring without any such change in airway pressure is considered to relate to an infant breath. In the event that pressure data from pneumotachometer and pressure transducer 56 is used instead of data from transducer 50, comparison is made between the breath volume and the data output by transducer 50 during the period of the breath. In this case the program detects a drop in pressure in tube 58 caused by ventilator 20 occluding tube 85.

A disk file is created and updated in real time with minute averages for a number of variables for use in the processing of data and calculation of flow rates, reports, etc. Illustrative of such variables are the time of day, tidal volume of the baby and its standard deviation, tidal volume of the ventilator, RR interval and its standard deviation, heart rate standard deviation, respiratory cycle time and its standard deviation, inspiratory time and its standard deviation, respiratory frequency and its standard deviation, respirator minimum pressure, respirator maximum pressure, airway mean pressure, short term variability (SDD) and its standard deviation, respiratory sinus arrhythmia (RSA), calibration gain factor, calibration time constant, zero flow, average of average blood pressure and its standard deviation, stystolic blood pressure and its standard deviation, diastolic blood pressure and its standard deviation and temperature of the infant, the air in the plethysmographic chamber, the inside wall of the plethysmographic chamber and the outside wall of the plethysmographic chamber.

Although the invention has been described as an apparatus and method wherein data is accumulated, processed and displayed on-line it will be apparent to those skilled in the art that an off-line data accumulation, processing and display system in which data is accumulated on a continuous basis for a predetermined period and is then loaded into a microcomputer system for processing, is equally contemplated by the invention. In this embodiment lines from the various transducers and monitors are coupled to an digital tape recorder which also receives a time stamp signal from a time marking device. This analog tape recorder subsequently inputs such data to a microcomputer system.

Figure 2:
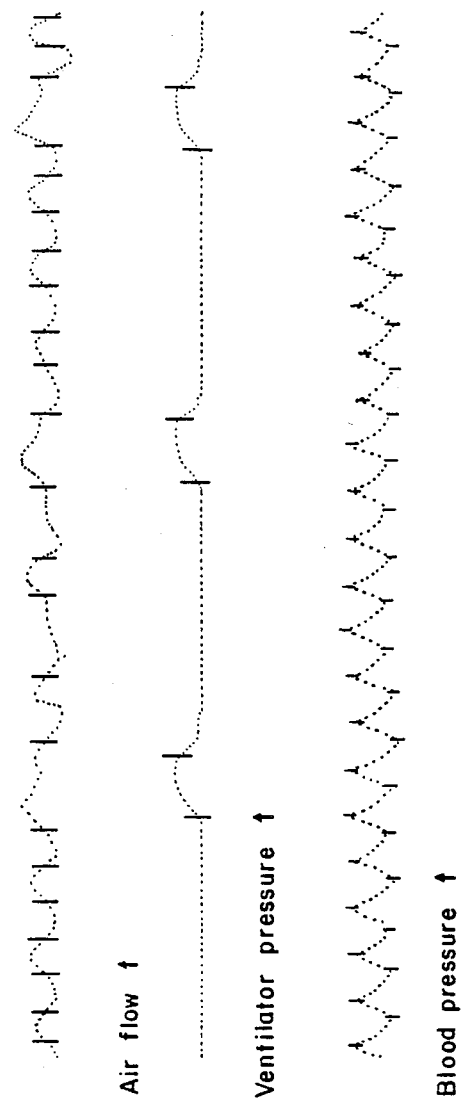
FIG. 2 is a real-time tracing of an infant's tidal air flow, airway pressure and arterial blood pressure.

Referring now to FIG. 2 there is depicted a real-time tracing of an infant's tidal air flow, airway pressure and arterial blood pressure. Appropriate blood pressure processing elements of the master program receive input in the form of digitized values of blood pressure. Such digitized values are obtained from known analog to digital conversion of the outputs available on typical commercial heart rate monitors. The digitized corrected and calibrated values are available as real-time tracings as shown in the lower tracing of FIG. 2. This figure also shows real-time tracings of airflow and airway pressure.

Figure 5:
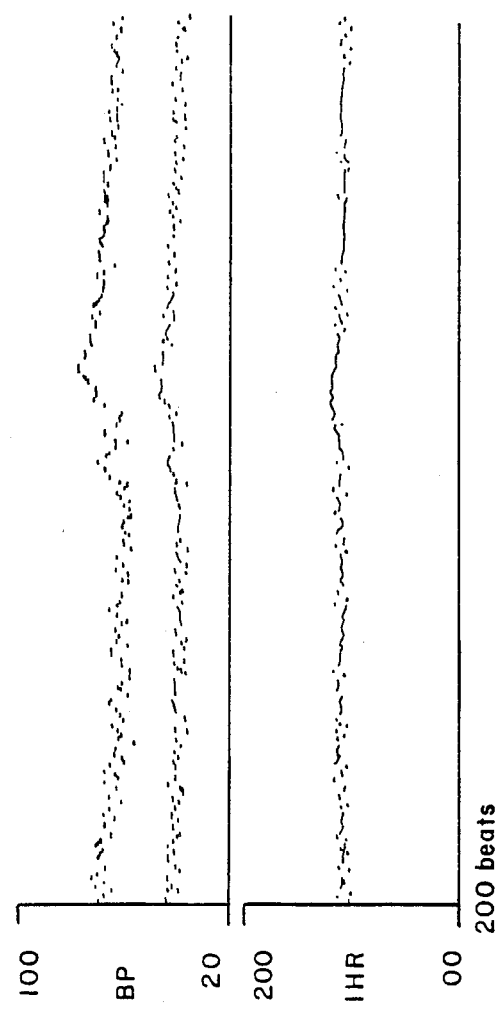
FIG. 5 is a tracing depicting the beat by beat instantaneous heart rate, systolic, diastolic, and mean blood pressure plotted over a user-selectable range, illustratively, 200 heart beats.

The program computes beat-to-beat systolic, diastolic and mean arterial pressures from the raw blood pressure signal. These beat-to-beat values are then plotted sequentially in a cardiorespiratory screen along with heart rate and tidal volume as depicted in FIG. 5. This display is very useful in summarizing the changes in vital signs during apnea or other acute events. The blood pressure values are also averaged each minute and displayed on the trend screen. This screen summarizes the changes in blood pressure during user selected intervals over time periods up to 24 hours in length. The user may choose to review a defined interval length, e.g. the preceding 30 minutes, 6 hours etc., or a specific period of clock-time, e.g. from 12:00 to 13:30. These data, and all other important patient data, are written to a disk file which accumulates a detailed history of the infant's clinical progress.

A pattern recognition algorithm is provided for detection of systolic and diastolic pressures in the blood pressure waveform. This process consists of two steps. Initially, the first derivative of the blood pressure waveform is examined for a positive then negative threshold. Then the maximum amplitude of the blood pressure waveform between these two points is located and taken to be the systolic pressure. Secondly the blood pressure waveform is examined between the currently located systolic pressure and the previous systolic pressure for a local minimum. This is taken to be the diastolic pressure.

Figure 3:
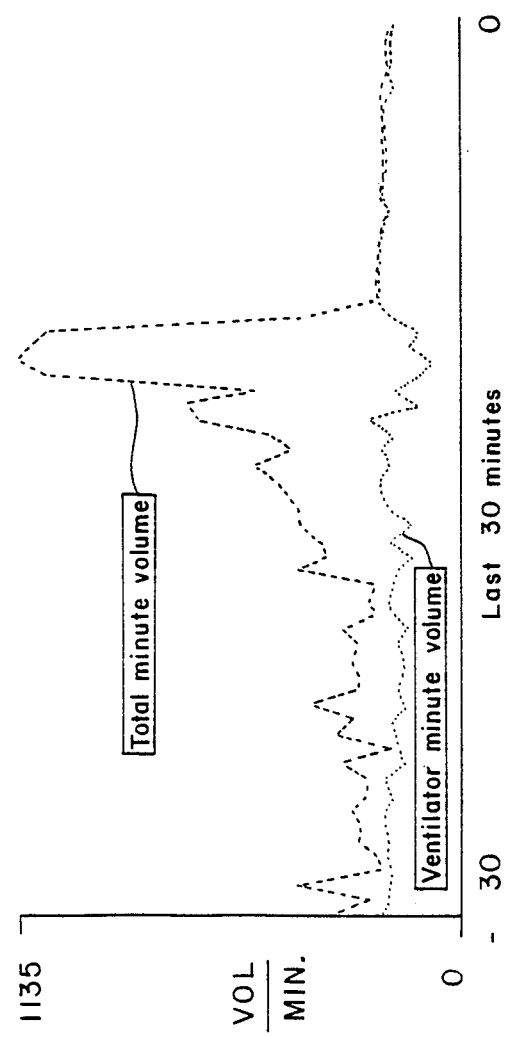
FIG. 3 is a tracing depicting an infant's total pulmonary ventilation, partitioned between the amount provided by the ventilator and the amount derived from the infant's own breathing efforts.

FIG. 3 is a tracing depicting an infant's total pulmonary ventilation, partitioned between the amount provided by the ventilator and the amount derived from the infant's own breathing efforts.

The pressure applied by the ventilator to the airway of the infant can be recorded by any of a variety of commercially available airway pressure monitors. The system uses the measurement of airway pressure for two reasons. First, it is important to quantify several parameters of the pressure pulse being applied to the airway of the patient, namely, peak pressure, trough pressure, mean pressure, respiratory cycle time, and the general shape of the pressure wave. The second use of the airway pressure measurement is to track the firing of the mechanical ventilator. When the airway pressure is observed to rise acutely, as it does when the ventilator delivers a pulse of air to the airway, the accompanying tidal volume is identified by the program and is recorded in the data file as a "ventilator" or "mechanical" breath. When breaths, i.e. patterned changes in airflow, are detected by the software, and these are not coincident with a ventilator pulse, the program files these as "infant" breaths.

By grouping tidal volumes into mechanical and infant subfiles the program is able to partition the total ventilation of the infant between that attributable to the infant's effort and that which is provided by the ventilator. In fact, the program computes the percent of the total volume provided by the mechanical ventilator on a continuous basis and displays this value on the ventilatory assistance screen as illustrated in FIG. 3.

An algorithm is also provided for detecting the presence of a pressure pulse in the airway pressure waveform. This process consists of several steps and will be discussed in detail in conjunction with FIG. 13. The first step is to locate the occurrence of a pressure pulse by examining the first derivative of the waveform for a positive threshold value followed by a negative threshold value. This indicates that an airway pressure pulse has occurred. The second step is to locate the end of the pressure pulse by examining the second derivative of the waveform for a local minimum between the positive and negative threshold values. This point corresponding to such local minimum is taken as the end of the pressure pulse from the ventilator. The start of the pressure pulse is determined by locating the local maximum in the second derivative of the pressure pulse waveform between the time of the positive threshold in the first derivative and a previous predetermined time interval, illustratively 0.5 seconds.

Figure 4:
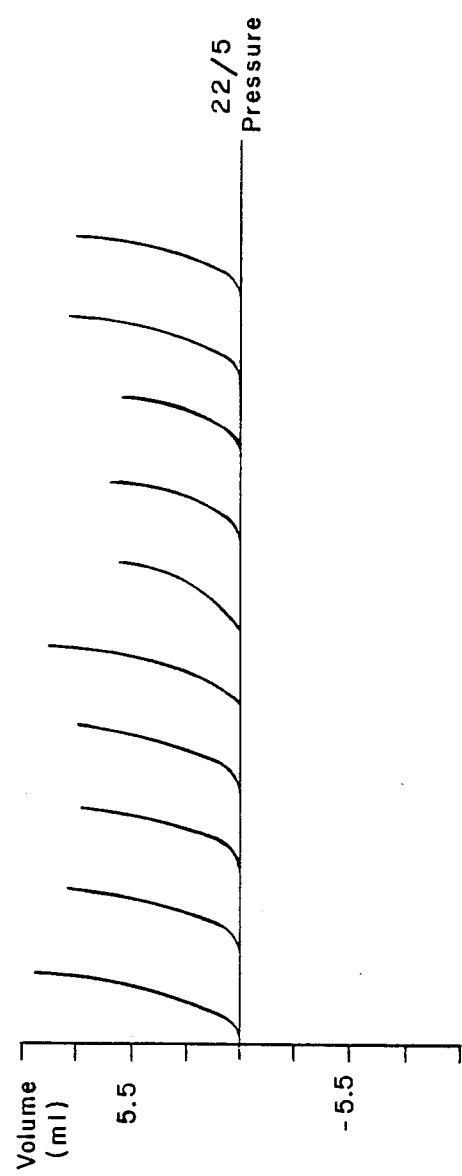
FIG. 4 is a tracing depicting the relationship between ventilator pressure and lung inflation for each ventilator pulse.

FIG. 4 is a tracing depicting the relationship between ventilator pressure and lung inflation for each ventilator pulse. As will be appreciated, changes in airway pressure are also related to the concomitant tidal flows and may be plotted, in real-time, as a continuous series of "pressure/volume inflation curves". The relationship between changes in airway pressure and changes in lung volume is an important indicator of pulmonary function. If substantial lung inflation occurs at low levels of airway pressure the lung is said to be compliant and, in general, healthy. If large pressures are required to inflate the lung it is noncompliant, and this is not healthy. The pressure-volume plots, which are displayed after each firing of the ventilator, are invaluable indices of the compliance of the lung, as depicted in FIG. 4. The effective compliance of the lung is calculated from the slope of this inflation curve and logged into the patient's data base. Thus, changes in the effective compliance of the lung can be easily related to other events and variables associated with the infant's care record.

Figure 7:
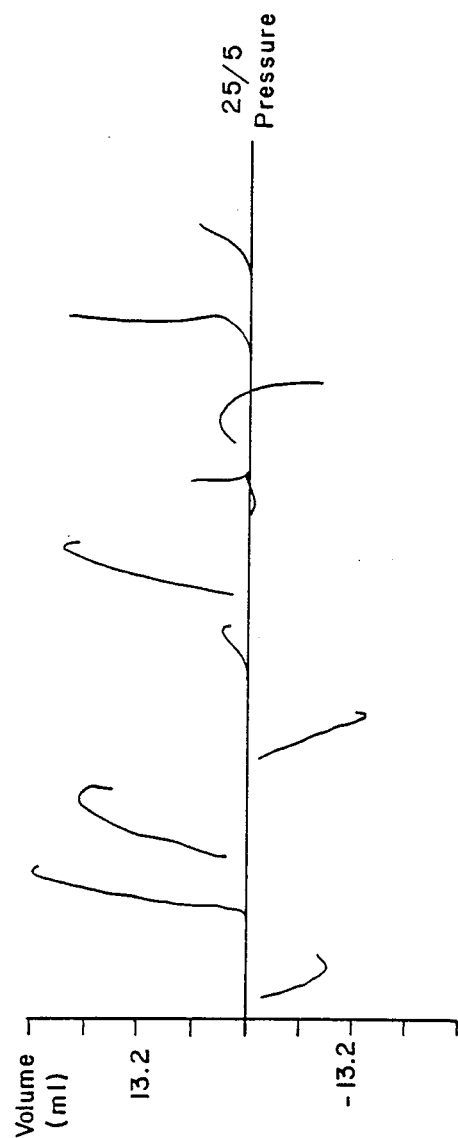
FIG. 7 is a tracing depicting the relationship between ventilator pressure and lung inflation for each ventilator pulse in which the infant is interacting unfavorably with the mechanical ventilator.

Additional important information about the interaction between the infant the mechanical ventilator is available from inspection of the "pressure-volume loops". When the infant is interacting favorably with the ventilator these loops take on a sigmoid, or S shaped appearance and the volume delivered by the machine is consistent from breath to breath. This type of favorable interaction is shown in FIG. 4. In contrast, these inflation curves can take on other much less desirable forms. Examples of these deviations can be seen in FIG. 7. These forms occur as a result of a mismatch between the infant's own breathing efforts and that provided by the ventilator. Large tidal volumes, and steep slopes are seen when infants breath in at the same time the ventilator fires. Thus, the volume is additive between the two and the lung is over-inflated. On the other hand, small tidal volumes are observed when the ventilator fires while the infant is exhaling. Occasionally the ventilator fires when the infant is exhaling forcefully and, in these instances, tidal volume is negative. This situation, known as "fighting" the ventilator, is extremely undesirable because pressure is built up as the ventilator forces air in to the lung while the infant is forcefully exhaling. This places the infant at risk for lung rupture or cerebral hemorrhage. Inspection of the form of the lung inflation curves allows the clinician to continuously monitor the synchrony between the infant and the ventilator. When this interaction appears unfavorable, appropriate changes in ventilator firing rate can be made, and using the continuous feedback provided by the present invention, the effectiveness of these changes can be readily evaluated. In alternative embodiments the present invention uses this ability to monitor infant/ventilator synchrony to develop a servomechanism for optimizing ventilator firing patterns.

Figure 6:
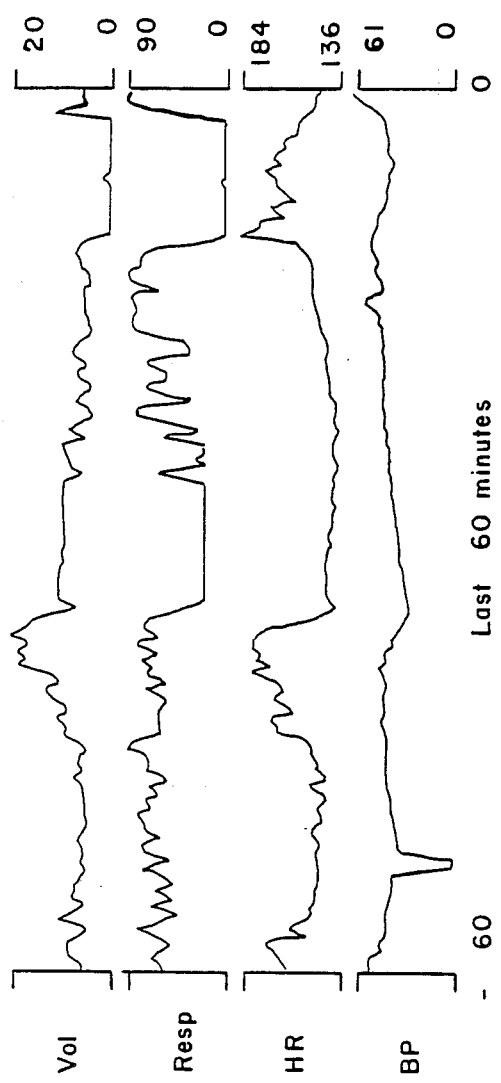
FIG. 6 is a tracing depicting trends of heart rate, blood pressure, minute volume, and respiratory rate over a user-selectable period of time, illustratively 60 minutes.

FIG. 6 is a tracing depicting trends of heart rate, blood pressure, minute volume, and respiratory rate over a user-selectable period of time. Such a period of time may be any suitable range, for example, the previous 60 minutes. Microcomputer System 130 advantageously outputs a wide variety of charts, displays, reports and the like. Illustratively, a display chart may indicate calibration measurement specifics, an infant's date of birth, age, weight and telephone number of parents. Any additional desired information may be provided on this display chart.

Minute by minute averages of the respiratory frequency, heart rate, blood pressure, etc. are preferably averaged over each hour. These hourly averages of patient history are used to compile a nursing shift report. A single summary sheet serves as a formal record of the major trends of the patient over each eight hour shift. This greatly reduces the amount of record keeping required of the nurses and frees them to attend to the patient rather than "paperwork".

Data recorded by the system is preferably related to the time of day and age of the infant. When a patient is placed in the plethysmograph, the clinician enters the following pertinent information; the infant's name, time and date of birth, telephone number of parents, and the patient's birth weight. As physiologic data is accumulated it is written, once each minute, into the data base in the proper time slot. Discontinuous signals such as daily weight, arterial blood gases, serum chemistries, etc. are manually entered at the keyboard and are entered into the data base at time specified. The data base, which is stored on a disk file, can be examined and edited by the user at any time off-line. In addition, with the aid of special purpose software, any of the variables can be plotted and analyzed further in an off-line mode. The data file is made available in a standard ASCII format which allows the raw data to be easily read by any of a variety of commercially available data base and statistical analysis software packages.

Figure 8:
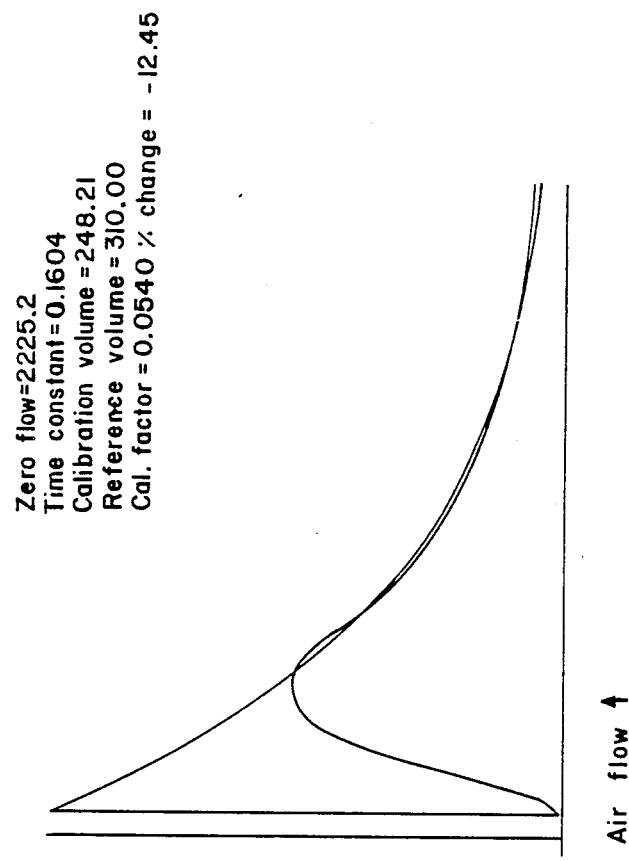
FIG. 8 depicts a tracing of an actual step response of a pressure pulse superimposed on a tracing of a step response derived from the actual step response.

FIG. 8 depicts an exponentially decreasing first waveform which represents an actual measured response of the system to a single pressure pulse from actuator 120, i.e., a response to an ideal step. FIG. 8 also depicts a second waveform, initially increasing, and then decreasing in an exponential manner. The second waveform is derived from the time constant of the system in accordance with the three steps previously disclosed. As will be appreciated, the two waveforms are very similar after an initial transitory period.

Figure 9:
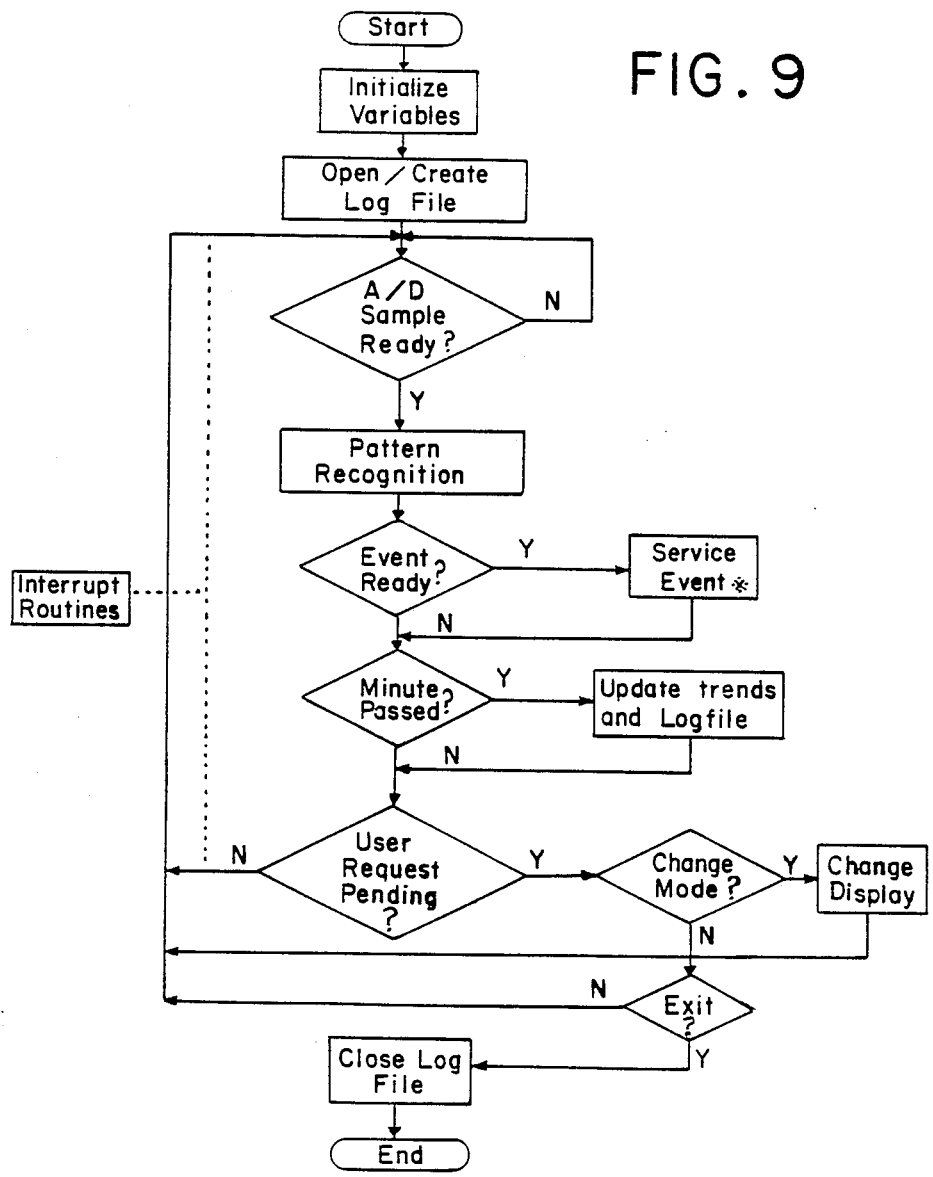
FIG. 9 is a flow chart depicting the main program loop control.
Figure 11:
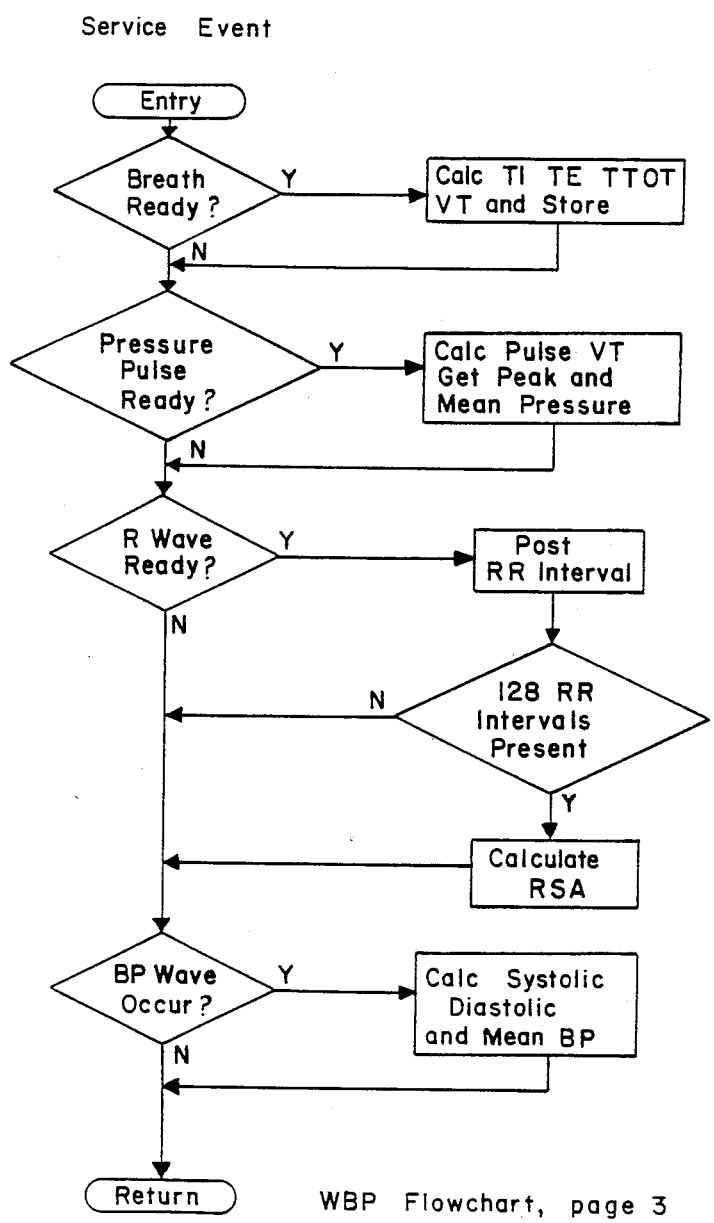
FIG. 11 is a flow chart depicting service events employed by the main program loop control of FIG. 9.

FIG. 9 is a flow chart depicting the main program loop control. Initially, system variables are initialized and a Log file is created. Once A/D samples are received pattern recognition software is run and detects patterns relating to air flow (FIG. 12), airway pressure (FIG. 13) and blood pressure (FIG. 14). Data indicative of these patterns and other useful data are provided to the computer system by differential pressure transducer 40, pressure transducer 50 and blood pressure, temperature and ECG monitoring devices as well as a pulse oximeter. Once an event is ready to be serviced, i.e., data collected and suitably processed or stored, an algorithm corresponding to the flow chart depicted in FIG. 11 is run. Such events illustratively include the RR interval, i.e., the distance between R-waves (spikes) on an ECG output waveform, inspiration cycle, pressure pulse, and systole measurement. For example, a breath cycle may be serviced by calculating inspiration (TI) and expiration (TE) times, total respiration cycle time ($TTOT = TI + TE$) and tidal volume (VT); a pressure pulse may be serviced by calculating the ventilator pressure pulse tidal volume (VT), its peak value and its mean pressure; a heart R wave may be serviced by calculating the respiratory sinus arrhythmia (RSA); and a blood pressure waveform may be serviced by calculating the systolic, diastolic and mean blood pressures. Once the events are serviced and an entire minute has not passed, the process is repeated until a minute has passed in which case the Log file is updated and an average calculation performed for illustrating trends on the system. A user request such as a mode or display change request may also be performed and provide a means for exiting the data gathering and processing process, if desired.

Figure 12:
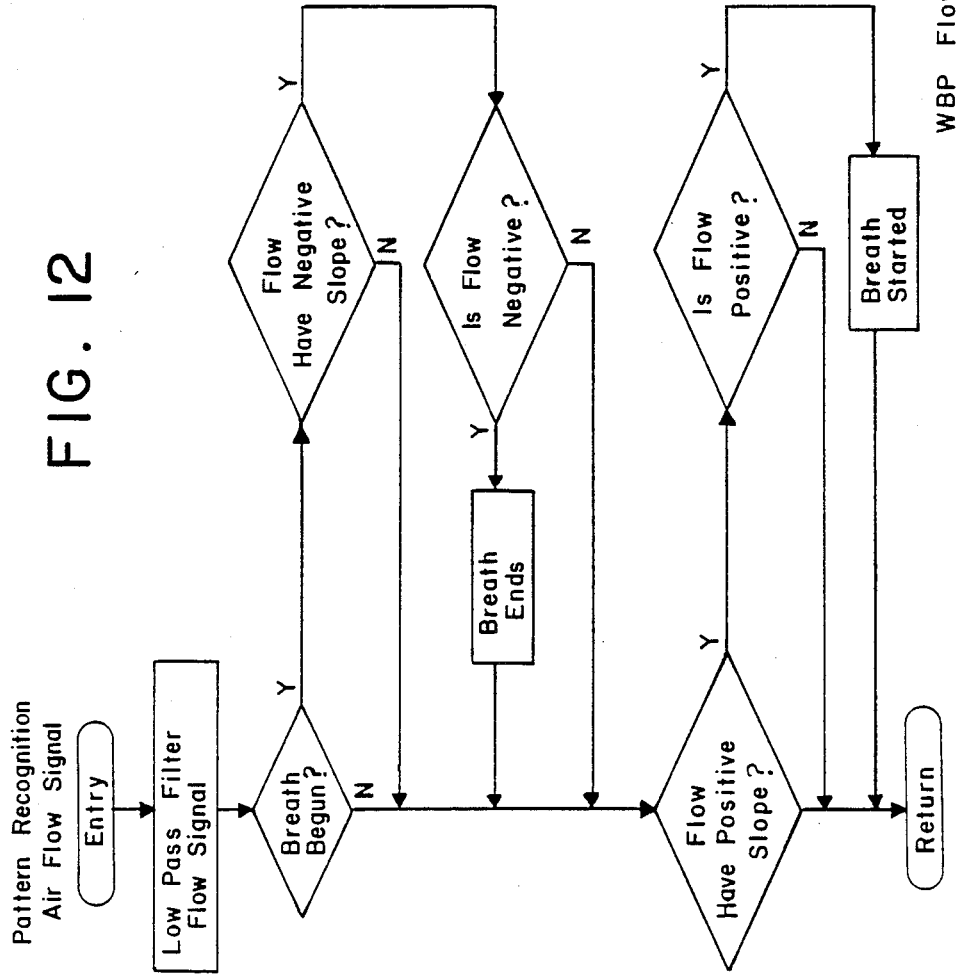
FIG. 12 is a flow chart depicting the pattern recognition for the air flow signal.

FIG. 12 depicts the air flow signal pattern recognition algorithm. In particular, once a breath has begun, a negative flow signal having a negative slope indicates that a breath is ending while a positive flow having a positive slope indicates that a breath has started.

Figure 13:
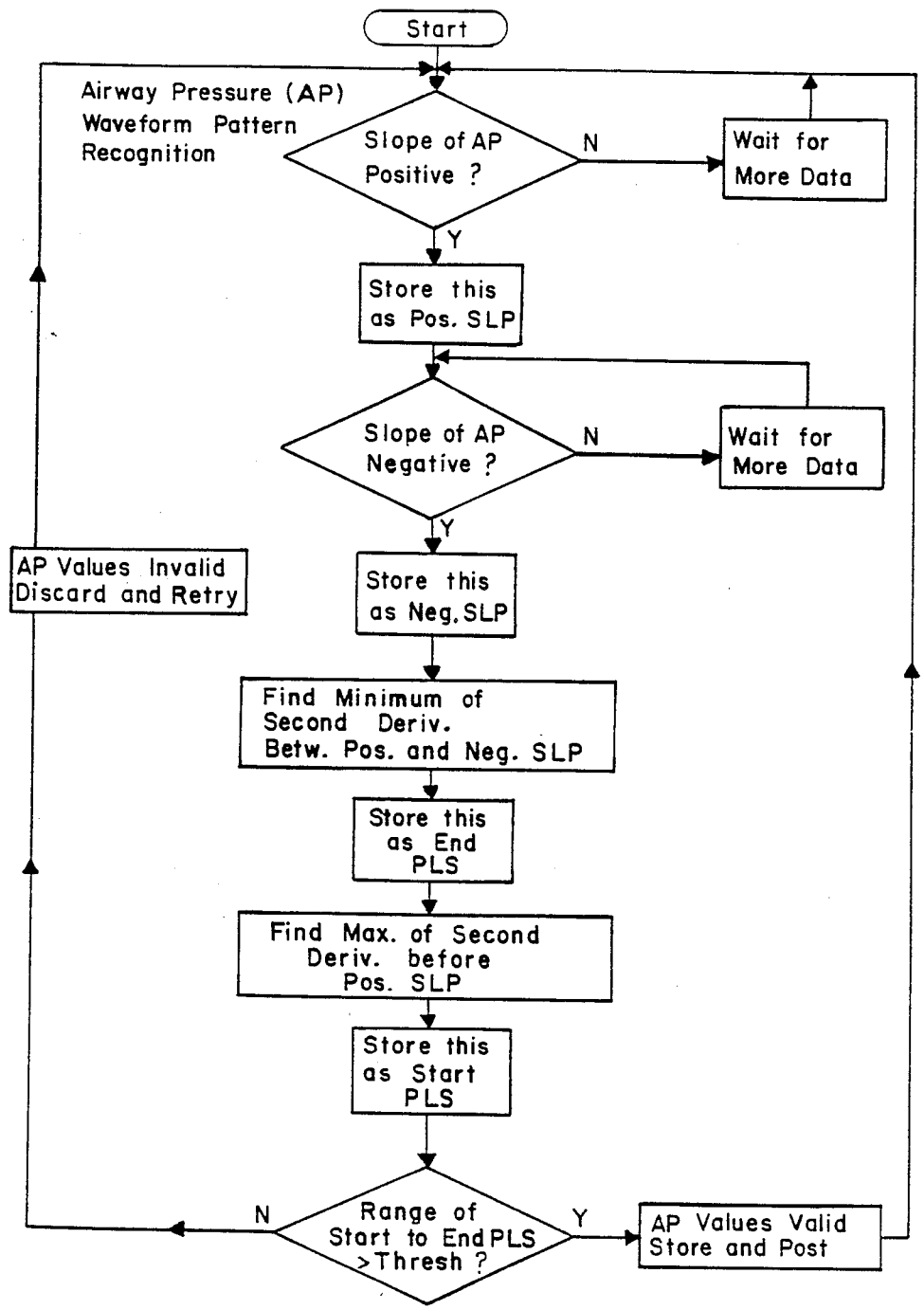
FIG. 13 is a flow chart depicting the airway pressure (AP) waveform.
Figure 14:
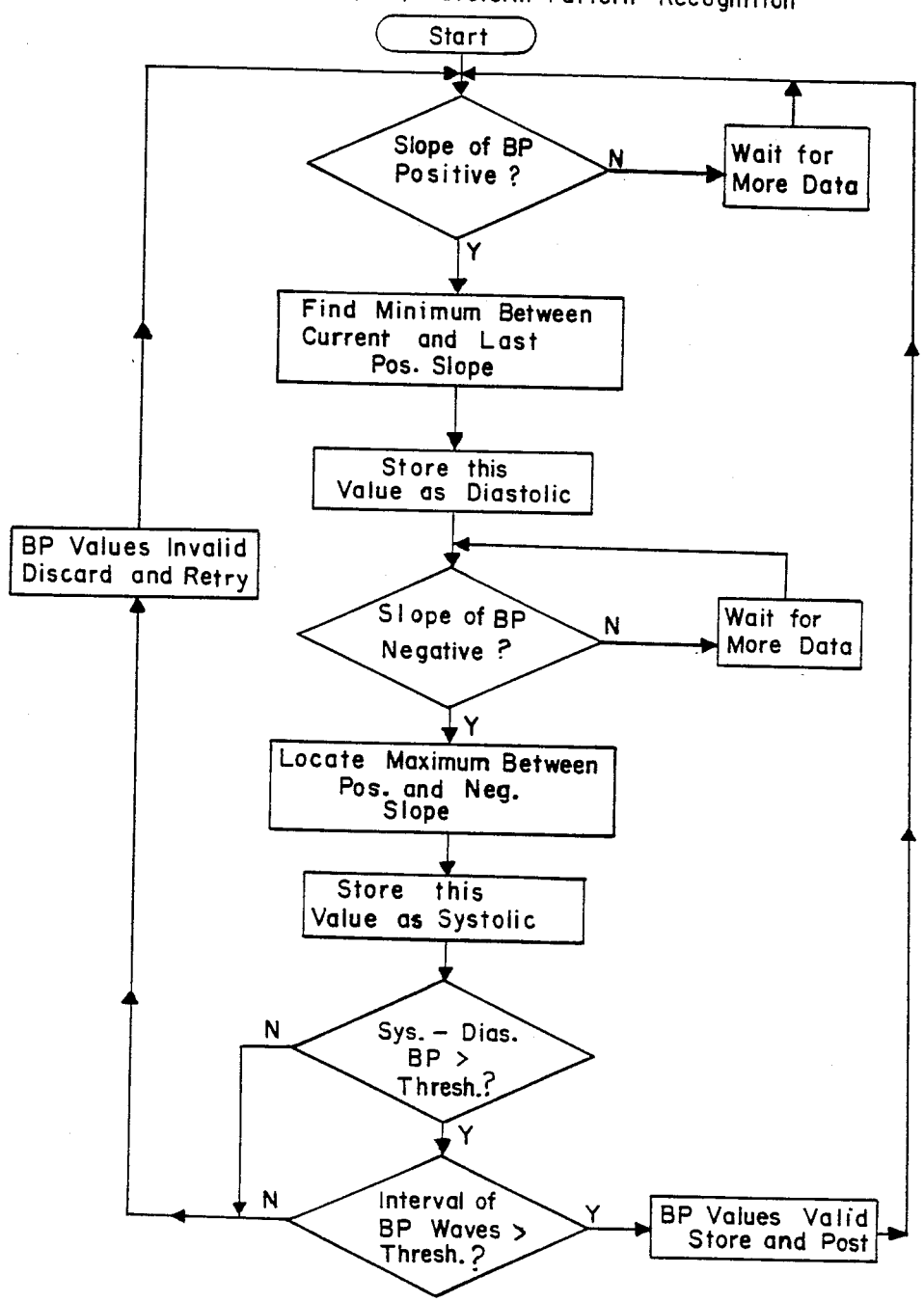
FIG. 14 is a flow chart depicting the blood pressure (BP) waveform.

FIG. 13 depicts the airway pressure (AP) waveform pattern recognition algorithm. In particular, once a threshold positive AP slope is encountered and stored, additional data is read until a threshold negative slope is encountered and stored. The minimum of the second derivative of this waveform between the points corresponding to the threshold positive encountered AP slope and the threshold negative encountered AP slope is determined and stored as the end of the pulse. Similarly, the maximum of the second derivative of the waveform before the threshold positive slope is determined and stored as the start of the pulse. If the range between the start and end of the pulse is greater than a predetermined threshold, the AP value is considered valid and stored, otherwise it is declared invalid. This process is repeated and a plurality of valid AP values are determined.

FIG. 14 depicts the blood pressure (BP) waveform pattern recognition algorithm. In particular, once a positive BP slope is encountered, the minimum value between the current and last positive slopes are calculated and stored as the diastolic. Once the BP slope becomes negative, the maximum value between the positive and negative slopes is determined and stored as the systolic. If the systolic minus the diastolic is not greater than a predetermined threshold, then the systolic and diastolic BP values are considered invalid and the procedure repeated. If the difference is greater, then the interval between blood pressure waves is examined. If such interval is not greater than a threshold, the systolic and diastolic BP values are considered invalid and the procedure repeated. If such interval is greater than a threshold, the systolic and diastolic values are considered valid and stored. This process is repeated and a plurality of valid BP systolic and diastolic values determined.

Figure 10:
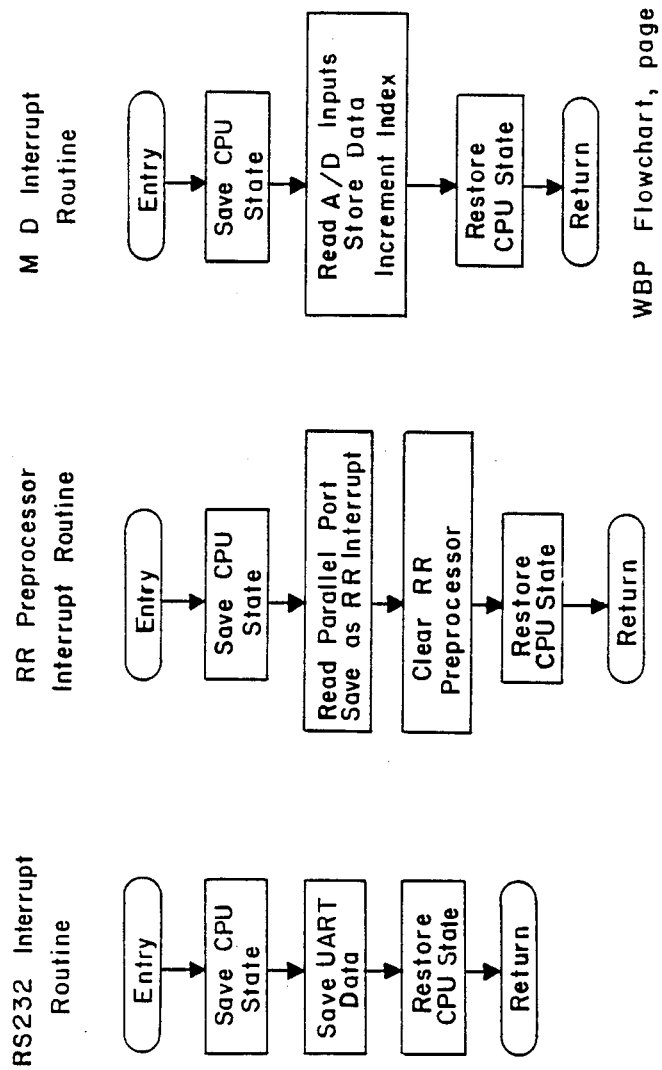
FIG. 10 is a flow chart depicting interrupt routines employed by the main program loop control of FIG. 9.
Figure 15:
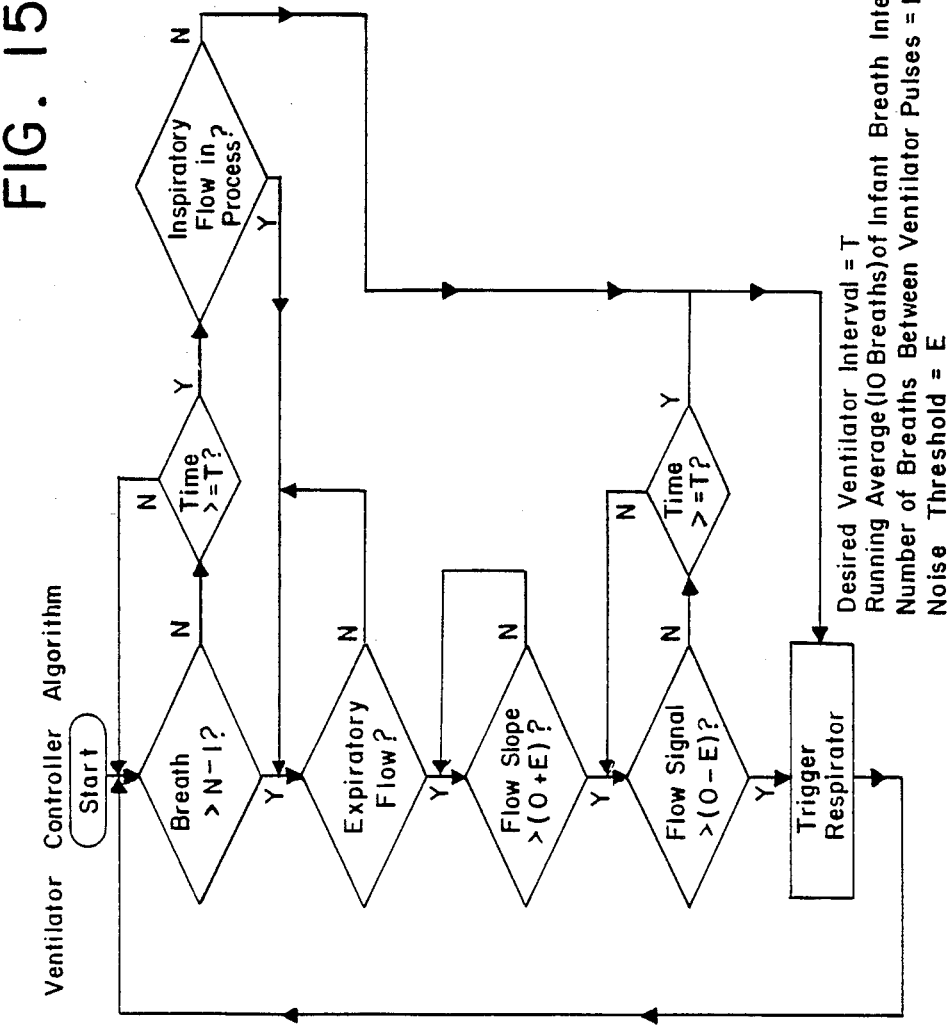
FIG. 15 is a flow chart depicting the ventilator controller algorithm.

FIG. 10 is a flowchart depicting the interrupt software for use with the master program of FIG. 9, while FIG. 15 is a flowchart of the algorithm for automatically controlling the rate of the ventilator, if desired. In particular, the number of breaths are counted until either the time for such counting equals or exceeds the desired ventilator interval or the number of breaths equals the average number of breaths N between ventilator pulses. If the number of breaths equals the average number of breaths between ventilator pulses or if the time is equal to or greater than N and an inspiratory flow is in process, a determination is made whether an expiratory flow has started. Once it has, and once the slope of the flow is greater than a threshold value, a determination is made whether the flow signal is greater than a threshold value. If the flow signal is greater than the threshold value or if it is not but a time greater than T has passed, the respirator is triggered. If it had been determined that an inspiratory flow was not in progress, the respirator would have been immediately triggered. Advantageously, this algorithm will produce lung inflation tracings more in accordance with FIG. 4 than FIG. 8. In other words, use of this algorithm will reduce the "fighting" between the infant's ventilation and the ventilator.

Appendix I is the object code of the software which controls the date acquisition, analyses, display, and logging functions of the present invention. This master program comprises a number of function modules. Each of these modules incorporates new data processing algorithms. Assuming the program is loaded starting at segment 123A, page 1 of Appendix I lists entry points in the form of segments and offsets (segment:offset) for various routines of the graphic display module, ventilation module, cardiovascular module and temperature module.

The graphic module provides for high resolution graphic displays to be sent to the central screen. The functions of this module are most easily understood by examining the various graphic outputs referred to in subsequent sections.

The ventilation module, using digitized outputs from the differential pressure transducer which monitors flow into and out of the plethysmograph, and the airway pressure sensor, provides analyses that link breathing efforts of the infant with the effects produced by the mechanical ventilator. More specifically, this module calculates airflow and displacement volume, airway pressure and pressure/volume relationships.

The cardiovascular module calculates blood pressure, heart rate and heart rate variability.

The temperature module calculates temperatures at, illustratively, a patient's skin, ambient air and two surfaces of the plethysmograph. These data are plotted on the temperature display for retrospective review of the thermostability of the patient and the environment.

While the invention has been described in conjunction with specific embodiments, it is evident in light of the foregoing description that numerous alternatives, modifications, and variations will be apparent to those skilled in the art.

We claim:

1. An apparatus for obtaining continuous measurements of infant ventilation during assisted ventilation by an assisted ventilation gas source comprising:
   a plethysmograph having at least an input port,
   means for coupling an assisted ventilation gas source to said input port of said plethysmograph,
   a pressure pulse source coupled to said plethysmograph for applying a pressure pulse of known volume into said plethysmograph,
   an endotracheal tube having a first end which is coupled to said input port and a second end which is insertable into an airway of an infant placed in said plethysmograph such that said airway is isolated from the interior of said plethysmograph,
   a pneumotachometer attached to said plethysmograph and having a resistance to air flow and being adapted for providing a pressure differential on opposite sides of said pneumotachometer,
   a differential pressure transducer coupled to said pneumotachometer for outputting a differential pressure signal reflecting said pressure differential, said differential pressure signal being proportional to a flow signal indicating a flow rate through said pneumotachometer,
   means for detecting pressure changes in said endotracheal tube caused by said assisted ventilation gas source and breathing efforts of said infant and for outputting an airway pressure signal in accordance with such pressure changes, means for converting said differential pressure signal into digital data, a preprogrammed computer system having:
means for calculating digitized flow data from said digitized differential pressure data,
means for frequency correcting said digitized flow data,
means for determining from said frequency corrected digitized data at least whether pressure changes in the interior of said plethysmograph are due to assisted ventilation or to the infant's breathing efforts and for determining a resultant volumetric displacement from said frequency corrected digitized flow data.

2. The apparatus of claim 1 further comprising means for gain correcting said digitized flow data.

3. The apparatus of claim 2 wherein said gain correcting means comprises means for integrating said digitized flow data and comparing said integrated flow data with a known volume displaced by activation of said pressure pulse source.

4. The apparatus of claim 3 wherein said pressure pulse source comprises a linear displacement actuator.

5. The apparatus of claim 1 further comprising a radiant heater located external to said plethysmograph and which radiates heat energy towards said plethysmograph and said infant and which produces convective heating within said plethysmograph.

6. The apparatus of claim 1 wherein said frequency correcting means comprises means for calculating a time constant of said plethysmograph and multiplying said time constant by a first derivative of said flow data with respect to time and adding the result to said flow data to provide frequency corrected flow data.

7. The apparatus of claim 6 wherein said time constant is the resistance of air flow openings in said plethysmograph multiplied by the compliance of air inside the plethysmograph.

8. The apparatus of claim 1 wherein said means for detecting pressure changes caused by said ventilation source comprises a pressure transducer adapted for sensing pressure in said endotracheal tube.

9. The apparatus of claim 8 wherein said pneumotachometer is positioned in an opening through a wall of said plethysmograph.

10. The apparatus of claim 1 wherein said means for detecting pressure changes caused by said ventilation source comprises:
a second pneumotachometer coupled to an exhaust port of said ventilator, and
a pressure transducer coupled to said second pneumotachometer.

11. The apparatus of claim 1 wherein said plethysmograph comprises a first section having a tapered edge and a second section hinged to said first section and sealable with said first section by way of a gasketing material placed on an edge of said second section for sealing contact with said tapered edge.

12. The apparatus of claim 11 further comprising means for moving said first section directly away from said second section to provide uniform sealing pressure between said tapered edge and said gasketing material.

13. The apparatus of claim 1 further comprising means for calculating systolic blood pressure and diastolic blood pressure of the infant.

14. The apparatus of claim 13 wherein said calculating means calculates a systolic pressure value by determining a maximum amplitude of a blood pressure waveform between a positive threshold value of a first derivative of said blood pressure waveform and a negative threshold value of said first derivative of said blood pressure waveform, said maximum amplitude being the diastolic pressure.

15. The apparatus of claim 14 wherein said calculating means calculates diastolic pressure by determining a local minimum of the blood pressure waveform between said systolic pressure value and a previous systolic pressure value, said local minimum being the diastolic pressure.

16. The apparatus of claim 1 further comprising means for synchronizing said infant's breath with said assisted ventilation.

17. A method for precisely calculating a flow rate of air into and out of a plethysmograph occasioned by breathing efforts of an infant and ventilatory assistance comprising:
measuring a difference in pressure across a pneumotachometer due to a flow rate into and out of said plethysmograph by a differential pressure transducer,
frequency correcting a signal output by said differential pressure transducer, said signal being proportional to said flow rate and said difference in pressure,
gain correcting the signal output by said differential pressure transducer,
wherein said frequency correcting and said gain correcting of said signal provides a gain and frequency corrected signal which precisely and accurately represents the flow of gas into and out of said infant's lungs.

18. The method of claim 17 wherein said frequency correcting comprises calculating a time constant of said plethysmograph and multiplying said time constant by a first derivative of said signal with respect to time and adding the result to said signal to provide a frequency corrected signal.

19. The method of claim 18 wherein said time constant is the resistance of air flow openings in said plethysmograph multiplied by the compliance of air inside the plethysmograph.

20. The method of claim 17 wherein said gain correcting comprises integrating said signal output by said differential pressure transducer and comparing said integrated signal with a known volume displaced by activation of a pressure pulse source coupled to said plethysmograph.

21. An improved plethysmograph of the type having a substantially enclosed plethysmographic chamber for receiving an infant, an assisted ventilation gas source coupled to said chamber, an endotracheal tube insertable into an airway of said infant, and means attached to said plethysmographic chamber for measuring airflow into and out of said plethysmographic chamber, wherein the improvement comprises a radiant heater external to said plethysmographic chamber which radiates heat towards said plethysmographic chamber thereby raising the temperature of said infant's skin and which also convectively heats said infant by heating air contained within said plethysmographic chamber, thereby accurately and precisely maintaining a desired temperature of said infant's skin.

22. An improved plethysmograph of the type having a substantially enclosed plethysmographic chamber for receiving an infant, an assisted ventilation gas source coupled to said chamber, an endotracheal tube insertable into an airway of said infant, and means attached to said plethysmographic chamber for measuring airflow into and out of said plethysmographic chamber, wherein the improvement comprises a linear displacement actuator coupled to said plethysmographic chamber for applying a pressure pulse of known volume into said plethysmograph.

23. An improved method of operating a plethysmograph of the type having a substantially enclosed plethysmographic chamber for receiving an infant, an assisted ventilation gas source coupled to said chamber, an endotracheal tube insertable into an airway of said infant, a pneumotachometer and a differential pressure transducer attached to said plethysmographic chamber, said transducer outputting a flow signal indicating a flow rate through said pneumotachometer, wherein the improvement comprises frequency correcting and gain correcting the flow signal output by said differential pressure transducer.

24. The improved method of claim 23 wherein said frequency correcting comprises calculating a time constant of said plethysmograph and multiplying said time constant by a first derivative of said flow signal with respect to time and adding the result to said flow signal to provide a frequency corrected flow signal.

25. The improved method of claim 24 wherein said time constant is the resistance of air flow openings in said plethysmograph multiplied by the compliance of air inside the plethysmograph.

26. The improved method of claim 25 wherein said gain correcting comprises integrating said flow signal output by said differential pressure transducer and comparing said integrated flow signal with a known volume displaced by activation of a pressure pulse source.

27. The improved method of claim 26 wherein said pressure pulse source displaces a known volume into and out of said plethysmograph.

28. An apparatus for obtaining continuous measurements of infant ventilation during assisted ventilation by an assisted ventilation gas source comprising:
a plethysmograph having at least an input port,
means for coupling an assisted ventilation gas source to said input port of said plethysmograph,
a pressure pulse source coupled to said plethysmograph for applying a pressure pulse of known volume into said plethysmograph,
an endotracheal tube having a first end which is coupled to said input port and a second end which is insertable into an airway of an infant placed in said plethysmograph such that said airway is isolated from the interior of said plethysmograph,
means for outputting a flow signal indicating a flow rate into and out of said plethysmograph,
means for detecting pressure changes in said endotracheal tube caused by said assisted ventilation gas source and breathing efforts of said infant and for outputting an airway pressure signal in accordance with such pressure changes,
means for converting said flow signal into a digital flow signal,
a preprogrammed computer system having:
means for calculating digitized flow data from said digitized flow signal,
means for frequency correcting said digitized flow data,
means for determining from said frequency corrected digitized data at least whether pressure changes in the interior of said plethysmograph are due to assisted ventilation or to the infant's breathing efforts and for determining a resultant volumetric displacement from said frequency corrected digitized flow data.

29. The apparatus of claim 28 wherein said means for outputting said flow signal comprises means adapted for creating a pressure differential between the interior of said plethysmograph and the exterior of said plethysmograph, and transducer means for outputting said flow signal which indicates a magnitude of said pressure differential.

30. The apparatus of claim 28 wherein said means for outputting said flow signal comprises:
a pneumotachometer attached to said plethysmograph and having a resistance to air flow and being adapted for providing a pressure differential on opposite sides of said pneumotachometer, and
a differential pressure transducer coupled to said pneumotachometer for outputting a differential pressure signal reflecting said pressure differential, said differential pressure signal being proportional to a flow signal indicating a flow rate through said pneumotachometer.

31. The apparatus of claim 28 further comprising means for gain correcting said digitized flow data.

32. The apparatus of claim 31 wherein said gain correcting means comprises means for integrating said digitized flow data and comparing said integrated flow data with a known volume displaced by activation of said pressure pulse source.

33. The apparatus of claim 28 further comprising a radiant heater located external to said plethysmograph and which radiates heat energy towards said plethysmograph and said infant and which produces convective heating within said plethysmograph.

34. The apparatus of claim 28 wherein said frequency correcting means comprises means for calculating a time constant of said plethysmograph and multiplying said time constant by a first derivative of said flow data with respect to time and adding the result to said flow data to provide frequency corrected flow data.

35. The apparatus of claim 34 wherein said time constant is the resistance of air flow openings in said plethysmograph multiplied by the compliance of air inside the plethysmograph.

36. The apparatus of claim 28 further comprising means for calculating systolic blood pressure and diastolic blood pressure of the infant.

37. The apparatus of claim 36 wherein said calculating means calculates a systolic pressure value by determining a maximum amplitude of a blood pressure waveform between a positive threshold value of a first derivative of said blood pressure waveform and a negative threshold value of said first derivative of said blood pressure waveform, said maximum amplitude being the diastolic pressure.

38. The apparatus of claim 37 wherein said calculating means calculates diastolic pressure by determining a local minimum of the blood pressure waveform between said systolic pressure value and a previous systolic pressure value, said local minimum being the diastolic pressure.

39. The apparatus of claim 28 further comprising means for synchronizing said infant's breath with said assisted ventilation.

40. An improved method of operating a plethysmograph of the type having a substantially enclosed plethysmographic chamber for receiving an infant, an assisted ventilation gas source coupled to said chamber, an endotracheal tube insertable into an airway of said infant, and means for producing a flow signal which indicates air flow into and out of said chamber, wherein the improvement comprises the steps of frequency correcting and gain correcting said flow signal output by said flow signal producing means.

41. The improved method of claim 40 wherein said frequency correcting step comprises calculating a time constant of said plethysmograph and multiplying said time constant by a first derivative of said flow signal with respect to time and adding the result to said flow signal to provide a frequency corrected flow signal.

42. The improved method of claim 41 wherein said time constant is the resistance of air flow openings in said plethysmograph multiplied by the compliance of air inside the plethysmograph.

43. The improved method of claim 42 wherein said gain correcting step comprises integrating said flow signal and comparing said integrated flow signal with a known volume displaced by activation of a pressure pulse source.

44. The improved method of claim 48 wherein said pressure pulse source displaces a known volume into and out of said plethysmograph.

* * * * *